US008227201B2

(12) United States Patent
Cooke et al.

(10) Patent No.: US 8,227,201 B2
(45) Date of Patent: Jul. 24, 2012

(54) BETA2-MICROGLOBULIN AND C REACTIVE PROTEIN (CRP) AS BIOMARKERS FOR PERIPHERAL ARTERY DISEASE

(75) Inventors: John P. Cooke, Palo Alto, CA (US); Andrew Wilson, Palo Alto, CA (US)

(73) Assignee: Board of Trustees of the Leland Stanford Junior University, Palo Alto, CA (US)

( * ) Notice: Subject to any disclaimer, the term of this patent is extended or adjusted under 35 U.S.C. 154(b) by 515 days.

(21) Appl. No.: 12/147,385

(22) Filed: Jun. 26, 2008

(65) Prior Publication Data

US 2009/0042214 A1 Feb. 12, 2009

Related U.S. Application Data

(60) Provisional application No. 60/946,681, filed on Jun. 27, 2007.

(51) Int. Cl.
 *G01N 33/53* (2006.01)
 *G01N 31/00* (2006.01)
(52) U.S. Cl. ............ 435/7.21; 435/2; 435/7.1; 436/501; 436/518; 436/522; 422/50; 530/300; 530/350
(58) Field of Classification Search .................. None
See application file for complete search history.

(56) References Cited

U.S. PATENT DOCUMENTS

2003/0149997 A1  8/2003  Hageman

FOREIGN PATENT DOCUMENTS

| EP | 1 615 036 A1 | 1/2006 |
| WO | WO-0106262 A1 | 1/2001 |
| WO | WO 2005/121758 A1 * | 12/2005 |
| WO | WO2005121758 | 12/2005 |
| WO | WO2007106466 | 9/2007 |
| WO | WO2008057966 | 5/2008 |

OTHER PUBLICATIONS

Saijo et al. (Hypertensive Research, vol. 28, No. 5, 2005, pp. 505-511).*
Criqui et al. (Vascular Medicine, 1998, vol. 3, pp. 241-245).*
Wilson et al., "BETA2-Microglobulin as a Biomarker in Peripheral Arterial Disease: Proteomic Profiling and Clinical Studies," Circulation, Sep. 18, 2007, vol. 116, pp. 1396-1403.
Tzoulaki, et al., C-Reactive protein, interleukin-6, and soluble adhesion molecules as predictors of progressive peripheral atherosclerosis in the general population:Edinburgh artery study, Circulation, (2005), vol. 112., pp. 976-981.
Aboyans V et al. "Risk factors for progression of peripheral arterial disease in large and small vessels." Circulation. Jun. 6, 2006;113(22):2623-9.
Beckman Ja et al. "Comparison of usefulness of inflammatory markers in patients with versus without peripheral arterial disease in predicting adverse cardiovascular outcomes (myocardial infarction, stroke, and death)." Am J Cardiol. Nov. 15, 2005;96(10):1374-8.
Boger Ca et al. "C-reactive protein as predictor of death in end-stage diabetic nephropathy: role of peripheral arterial disease." Kidney Int. Jul. 2005;68(1):217-27.
Depalma Rg et al. "Statins and biomarkers in claudicants with peripheral arterial disease: cross-sectional study." Vascular. Jul.-Aug. 2006; 14(4):193-200.
Ferrante G. "C-reactive protein in peripheral arteriopathies (its relation to alpha 2-globulin, alpha 2-glycoprotin and Winzler's seromucoid)." Acta Med Ital Mal Infett Parassit. Dec. 1959;14:345-7. Italitan.
Liu J et al. "Lysosomal cysteine proteases in atherosclerosis." Arterioscler Thromb Vasc Biol. Aug. 2004;24(8):1359-66.
Garg Pk et al. "Physical activity during daily life and mortality in patients with peripheral arterial disease." Circulation. Jul. 18, 2006;114(3):242-8.
Hampel D et al. "Toward Proteomics in Uroscopy: Urinary Protein Profiles after Radiocontrast Medium Administration." J Am Soc Nephrol 2001, 12:1026-1035.
Hozawa A et al. "C-reactive protein and peripheral artery disease among Japanese elderly: the Tsurugaya Project." Hypertens Res. Dec. 2004;27(12):955-61.
Iwashima Y et al. "Adiponectin and inflammatory markers in peripheral arterial occlusive disease." Atherosclerosis. Oct. 2006;188(2):384-90.
Kaperonis Ea et al. "Inflammation and Chlamydia pneumoniae infection correlate with the severity of peripheral arterial disease." Eur J Vasc Endovasc Surg. May 2006;31(5):509-15.
Karlsson H et al. "Lipoproteomics I: Mapping of proteins in low-density lipoprotein using two dimensional gel electrophoresis and mass spectrometry." Proteomics 2005, 5;551-565.
Kimura E et al. "Proteomic profiling reveals the plasma beta 2 microglobulin is a potential marker for PAD." Vascular Medicine 2006; 11:S1-S17.
Kimura E et al. "Application of microarray bioinformatics approaches to proteomic profiling in PAD." Vascular Medicine 2005; 10:123-174.
Koo Bk et al. "C-reactive protein in stable angina patients without peripheral vascular disease." Int J Cardiol. Mar. 2003;88(1):105-6.
Mcdermott Mm et al. "D-dimer and inflammatory markers as predictors of functional decline in men and women with and without peripheral arterial disease." J Am Geriatr Soc. Oct. 2005;53(10):1688-96.
Mcdermott Mm et al. "Inflammatory markers, D-dimer, prothrombotic factors, and physical activity levels in patients with peripheral arterial disease." Vasc Med. May 2004;9(2):107-15.
Mcdermott Mm et al. "Patterns of inflammation associated with peripheral arterial disease: the InCHIANTI study." Am Heart J 2005;150:276-81.
Musicant Se et al. "Prospective evaluation of the relationship between C-reactive protein, D-dimer and progression of peripheral arterial disease." J Vasc Surg. Apr. 2006;43(4):772-80.
Nair N et al. "Use of SAM (significance analysis of microarrays) in proteomic profiling of peripheral arterial disease." Vascular Medicine 2005;10:123-174.

(Continued)

*Primary Examiner* — Lisa Cook
(74) *Attorney, Agent, or Firm* — Edwards Wildman Palmer LLP; Peter F. Corless; Andrew W. Shyjan, Esq.

(57) ABSTRACT

The present invention relates to use of β-2-microglobulin (B2M or β2M) and C-reactive protein (CRP) levels as biomarkers of peripheral artery disease and/or atherosclerosis.

11 Claims, 6 Drawing Sheets

OTHER PUBLICATIONS

Nedelkov D et al. "Design and use of multi-affinity surfaces in biomolecular interaction analysis-mass spectrometry (BIA/MS): a step toward the design of SPR/MS arrays," Journal of Molecular Recognition, 2003, 16:15-19.

O'Hare, Am et al. "Cystatin C and incident peripheral arterial disease events in the elderly." Arch. Intern. Med., 2005, 165 :2666-2670.

Owens Cd et al. "Elevated C-reactive protein levels are associated with postoperative events in patients undergoing lower extremity vein bypass surgery." J Vasc Surg. Jan. 2007;45(1):2-9. discussion 9.

Paladino L et al. "The C-reactive protein in the serum and liquid of bullae of arteriopathic patients." Rass Int Clin Ter. Oct. 31, 1960;40:1129-33.

Ridker Pm et al. "Novel risk factors for systemic atherosclerosis: a comparison of C-reactive protein, fibrinogen, homocysteine, lipoprotein(a), and standard cholesterol screeing as predictors of peripheral arterial disease." JAMA. May 16, 2001;285(19):2481-5.

Ridker Pm et al. "Plasma concentration of C-reactive protein and risk of developing peripheral vascular disease." Circulation. Feb. 10, 1998;97(5):425-8.

Rossi et al. Risk of myocardial infarction and angina in patients with severe peripheral vascular disease: predictive role of C-reactive protein. Circulation. Feb. 19, 2002;105(7):800-3.

Saijo Y et al. "Relationship of beta2-microglobulin to arterial stiffness in Japanese subjects." Hypertens Res 2005;28:505-11.

Schillinger M et al. "Joint effects of C-reactive protein and glycated hemoglobin in predicting future cardiovascular events of patients with advanced atherosclerosis." Circulation AHA Journals, Nov. 2003:2323-2328.

Schillinger M et al. "Endovascular revascularization below the knee: 6-month results and predictive value of C-reactive protein level." Radiolovy. May 2003;227(2):419-25.

Shinkai S et al. "Beta2-microglobulin for risk stratification of total mortality in the elderly population: comparision with cystatin C and C-reactive protein." Arch Intern Med. Jan. 28, 2008;168(2):200-6.

Standl E et al. "Predictors of 10-year macrovascular and overall mortality in patients with NIDDM: the Munich General Practioner Project," Diabetologia, 1996, 39:1540-1545.

Stuveling Em et al. "C-reactive protein and microalbuminuria differ in their associations with various domains of vascular disease." Atherosclerosis. Jan. 2004;172(1):107-14.

Tataranni G et al. "Beneficial effects of verapamil in renal-risk surgical patients." Ren Fail. 1994;16(3):383-90.

Thongboonkerd V et al. "Proteomic analysis reveals alterations in the renal Kallikrein pathway during hypoxia-induced hypertension," J. Biol. Chem., 2002, 277(38):34708-34716.

Tzoulaki I et al. "C-reactive protein, interleukin-6, and soluble adhesion molecules as predictors of progressive peripheral atherosclerosis in the general population: Edinburgh Artery Study." Circulation. Aug. 16, 2005;112(7):976-83.

Tzoulaki I et al., "Hemostatic factors, inflammatory markers, and progressive peripheral atherosclerosis: the Edinburgh Artery Study." Am J Epidemiol. Feb. 15, 2006;163(4):334-41.

Unlu Y et al. "Comparison of levels of inflammatory markers and hemostatic factors in the patients with and without peripheral arterial disease." Thromb Res. 2006;117(4):357-364.

Vainas T et al. "C-reactive protein in peripheral arterial disease: relation to severity of the disease and to future cardiovascular events." J Vasc Surg. Aug. 2005;42(2):243-51.

Vu Jd et al. "Impact of C-reactive protein on the likelihood of peripheral arterial disease in United States adults with the metabolic syndrome, diabetes mellitus, and preexisting cardiovascular disease." Am J Cardiol. Sep. 1, 2005;96(5):655-8.

Wildman Rp et al. Relation of inflammation to peripheral arterial disease in the national health and nutrition examination survey, 1999-2002. Am J Cardiol. Dec. 1, 2005;96(11):1579-83.

Wilson Am et al. Beta 2 microglobulin as a biomarker in peripheral arterial disease: proteomic profiling and clinical studies. Circulation. 2007;116:1396-1403.

Yu Hi et al. "C-reactive protein and risk factors for peripheral vascular disease in subjects with Type 2 diabetes mellitus." Diabet Med. Apr. 2004;21(4):336-41.

Zumrutdal Al et al. "Atherosclerosis in haemodialysis patients without significant comorbidities: determinants of progression." Nephrology (Carlton). Dec. 2006;11(6):489-93.

Zumrutdal Al et al. "Cardiac tropinin I and beta 2 microglobulin as risk factors for early-onset atherosclerosis in patients on haemodialysis." Nephrology 2005, 10:453-458.

Tusher Vg et al. "Significance analysis of microarrays applied to the ionizing radiation response." Pro Natl Acad Sci USA. Apr. 24, 2001;98(9):5116-5121.

* cited by examiner

A

Fractionated Plasma

Unfractionated Plasma

|  | Area Under Curve |
|---|---|
| β 2 Microglobulin | 0.627 |
| Hs CRP | 0.603 |
| β 2 Microglobulin & Hs CRP | 0.641 |

BETA2-MICROGLOBULIN AND C REACTIVE PROTEIN (CRP) AS BIOMARKERS FOR PERIPHERAL ARTERY DISEASE

CROSS-REFERENCE TO RELATED APPLICATION

This application claims priority benefit of U.S. provisional application Ser. No. 60/946,681, filed Jul. 27, 2007, which application is incorporated herein by reference in its entirety.

STATEMENT REGARDING FEDERALLY SPONSORED RESEARCH

This invention was made with government support under grant no. 5RO1 HL075774 awarded by the National Institutes of Health. The federal government has certain rights in this invention.

BACKGROUND OF THE INVENTION

Atherosclerosis is a complex process which is generally associated with deposition of fats, cholesterol, fibrin, platelets, cellular debris and calcium, and accompanying formation of plaques, on the luminal wall of vascular endothelial cells. The innermost layer of the artery becomes markedly thickened by these accumulating cells and surrounding material. Sufficient thickening of the arterial wall results in reduction of the diameter of the artery, severely diminishing vascular flow to target organs, leading to morbidity and mortality. The distribution of atherosclerotic plaques is broadly divided into the coronary arteries and the peripheral circulation (most commonly, the lower extremities). Some individuals are primarily affected in the coronary arteries (causing coronary artery disease, "CAD"), in the peripheral arteries (causing peripheral artery disease, "PAD"), while other individuals are substantially affected in both regions. Risk factors for PAD include smoking, hyperlipidemia, hypertension, diabetes, and family history. Untreated PAD can lead to decreased mobility, ulcers, gangrene, and may ultimately require amputation of the affected extremity.

Because of compensatory mechanisms that exist in normal physiologic responses, clinical symptoms of CAD and PAD may not present themselves until the disease has progressed to severe levels. No effective screening tests exist. Both CAD and PAD can be quantified using invasive techniques such as angiography. PAD may be quantitated using a Doppler ultrasound to measure the ankle-brachial index ("ABI"), which entails calculating the ratio of the systolic reading of the pressure in the upper extremity versus the lower extremity. In most healthy individuals, the ratio approaches or is at about 1 (i.e., 0.90 or greater) while in patients with a ratio less than 0.90, PAD is diagnosed. Generally, the lower the ratio, the more severe the disease.

The measurement of the ankle-brachial index is not generally practiced, leading to the under-diagnosis of PAD. Moreover, in patients with diabetes, who constitute greater than 20% of patients with PAD, poor vascular compressibility may cause the ABI test to yield false negatives. Furthermore, ABI does not accurately distinguish PAD patients from long claudicator ("LC") PAD patients who may have somewhat milder forms of PAD, at least as measured by the decreased pain experienced by LC patients during and after exercise. PAD, when diagnosed early, is amenable to treatments which slow progression of the disease.

Literature

Saijo et al. "Relationship of beta2-microglobulin to arterial stiffness in Japanese subjects." Hypertens Res 2005 28 505-11

WO 05/121758; WO 05/007890; U.S. application Ser. No. 11/685,146, filed Mar. 12, 2007; and international application no. PCT/US07/06276, filed Mar. 12, 2007.

Kinlay et al. "Inflammatory markers in stable atherosclerosis" Am J. Cardiol. 2006 Dec. 4; 98(11 S1):S2-S8. Epub 2006 Sep. 28;

Tsimikas et al. "C-reactive protein and other emerging blood biomarkers to optimize risk stratification of vulnerable patients." J Am Coll Cardiol. 2006 Apr. 18; 47(8 Suppl): C19-31;

Hozawa et al. "C-reactive protein and peripheral artery disease among Japanese elderly: the Tsurugaya Project." Hypertens Res. 2004 December; 27(12):955-61;

Okamura et al. "Non-invasive measurement of brachial-ankle pulse wave velocity is associated with serum C-reactive protein but not with alpha-tocopherol in Japanese middle-aged male workers." Hypertens Res. 2004 March; 27(3): 173-80;

Vu et al. "Impact of C-reactive protein on the likelihood of peripheral arterial disease in United States adults with the metabolic syndrome, diabetes mellitus, and preexisting cardiovascular disease." J. Cardiol. 2005 Sep. 1; 96(5): 655-8;

Elgahrib et al. "C-reactive protein as a novel biomarker. Reactant can flag atherosclerosis and help predict cardiac events." Postgrad Med. 2003 December; 114(6):39-44;

Schillinger et al. "Joint effects of C-reactive protein and glycated hemoglobin in predicting future cardiovascular events of patients with advanced atherosclerosis." Circulation. 2003 Nov. 11; 108(19):2323-8. Epub 2003 Oct. 13.

SUMMARY OF THE INVENTION

The present invention relates to use of $\beta$-2-microglobulin (B2M or $\beta$2M) and C-reactive protein (CRP) levels as biomarkers of peripheral artery disease and/or atherosclerosis.

In one aspect the disclosure features a method for classifying peripheral artery disease status in a subject comprising: detecting a level of beta-2-microglobulin (B2M) in a blood sample from a subject, wherein the subject has one or more cardiovascular disease symptoms or risk factors; and detecting a level of C-reactive protein (CRP) in a blood sample from the subject, wherein levels of B2M and CRP detected are indicative of a peripheral artery disease (PAD) status in the subject. In related embodiments, the CRP and B2M levels are detected by immunoassay and/or by mass spectrometry. In further related embodiments, the blood sample is peripheral blood or a blood derivative. The CRP and B2M levels can be analyzed by executing a software classification algorithm. In certain embodiments, the method further comprises reporting a PAD status of the subject and/or managing treatment of the subject in response to the PAD status. In certain embodiments, the subject of the method has been diagnosed with coronary artery disease.

The disclosure further discloses methods for diagnosing peripheral artery disease (PAD) in a subject having coronary artery disease (CAD), the method comprising detecting a level of beta-2-microglobulin (B2M) in a biological sample from a subject, wherein the subject has one or more symptoms or risk factors common to peripheral artery disease (PAD) and coronary artery disease (CAD); and detecting a level of C-reactive protein (CRP) in the biological sample from the subject, wherein the levels of B2M and CRP detected are indicative of a diagnosis of PAD in the subject.

The disclosure further provides methods for assessing a course of peripheral artery disease comprising detecting at a first time a level of beta-2-microglobulin (B2M) and a level of C reactive protein (CRP) in a first biological sample from a subject having peripheral artery disease (PAD); and detecting at a second time a level of beta-2-microglobulin (B2M) and a level of C reactive protein (CRP) in a second biological sample from a subject, wherein the presence of absence of an increase or decrease in the B2M and CRP levels at said second time relative to said first time is indicative of the course of the peripheral artery disease.

The disclosure also provides methods for selecting an agent that concordantly modulates beta-2-microglobulin (B2M) and C-reactive protein levels in a subject, wherein the method comprises administering an agent to a subject having one or more peripheral artery disease (PAD) symptoms or risk factors; and assessing a beta-2-microglobulin (B2M) level and a C-reactive protein (CRP) level following administering, wherein the presence of absence of a concordant change in the B2M level and the CRP level in the subject after said administering relative to a B2M level and a CRP level prior to said administering indicates whether the agent concordantly modulates B2M and CRP levels.

In further aspects the disclosure provides kits comprising a solid support comprising a capture reagent that binds beta-2-microglobulin (B2M); a solid support comprising a capture reagent that binds C reactive protein (CRP); and instructions for using the solid support to detect beta-2-microglobulin and CRP. In related embodiments, the capture reagent that binds B2M and the capture reagent that binds CRP are provided on the same solid support. In other related embodiments, the kit further comprising a standard reference for B2M and a standard reference for CRP.

The disclosure further provides a software product comprising code that accesses data attributed to a sample, the data comprising detection of a level of at least two biomarkers in the sample, wherein the at least two biomarkers include beta-2-microglobulin (B2M) and C-reactive protein (CRP); and code that executes a classification algorithm that classifies the peripheral artery disease status of the sample as a function of said detection.

The disclosure also provides a computerized system for classifying peripheral artery disease status in a subject comprising an input device for entering a first value for a CRP level and a second value for a B2M level, wherein the first and second values are obtained from assaying one or more samples from a patient; a computer operably linked to the input device and comprising a computer readable medium comprising an executable program that executes a classification algorithm that classifies the peripheral artery disease status of the patient based on the first and second values entered through the input device, wherein the first and second values are indicative of the peripheral artery disease (PAD) status of the patient; and a display operably linked to the computer, wherein results of application of the classification algorithm are display as a report to the user.

In another aspect, the disclosure provides a computerized system for classifying peripheral artery disease status in a subject comprising an input device for entering a first value for a C-reactive protein level (CRP) level and a second value for a beta-2 microglobulin level, wherein the first and second values are obtained from assaying one or more samples from a patient; a computer operatively linked to the input device and comprising a computer readable medium comprising an executable program that executes a classification algorithm that classifies the peripheral artery disease status of the patient based on the first and second values entered through the input device, wherein the first and second values are indicative of the peripheral artery disease (PAD) status of the patient; and a display operatively linked to the computer, wherein results of application of the classification algorithm are display as a report to the user to provide an indication of the PAD status of the patient.

These and other embodiments of the invention will be readily apparent to the ordinarily skilled artisan upon reading the present specification.

BRIEF DESCRIPTION OF THE DRAWINGS

FIGS. 2A-2B: Index ABI and ACT compared to total peak intensities of 12 kDa proteins in subjects with or without PAD. Peak intensities of the six 12 kDa protein for the groups characterized by: FIG. 2A. ABI (ABI<0-9, n=44; 0-9>ABI>0-6, n=23; ABI<0-6, n=21). Differences between groups compared by one-way ANOVA with Bonferroni correction. FIG. 2B. ACT (Control, n=43, ie. no claudication during exercise; ACT>12 minutes, n=6; ACT<12 minutes, n=39) Total peak intensities are represented as relative intensity units. Differences between groups compared by one-way ANOVA with Bonferroni correction. Error bars show standard deviations.

FIG. 3, Panel A. The region of the mass spectra around 12 kDa is expanded and aligned, for each of 4 control (1-4) and 4 PAD subjects (5-8). The β2m peaks are indicated by the arrow. FIG. 3, Panel B. Fractionated plasma at pH 5-0 and unfractionated plasma from the same eight patients were analyzed with Western blot analysis with anti-β2m antibody.

DEFINITIONS

Figure 1:
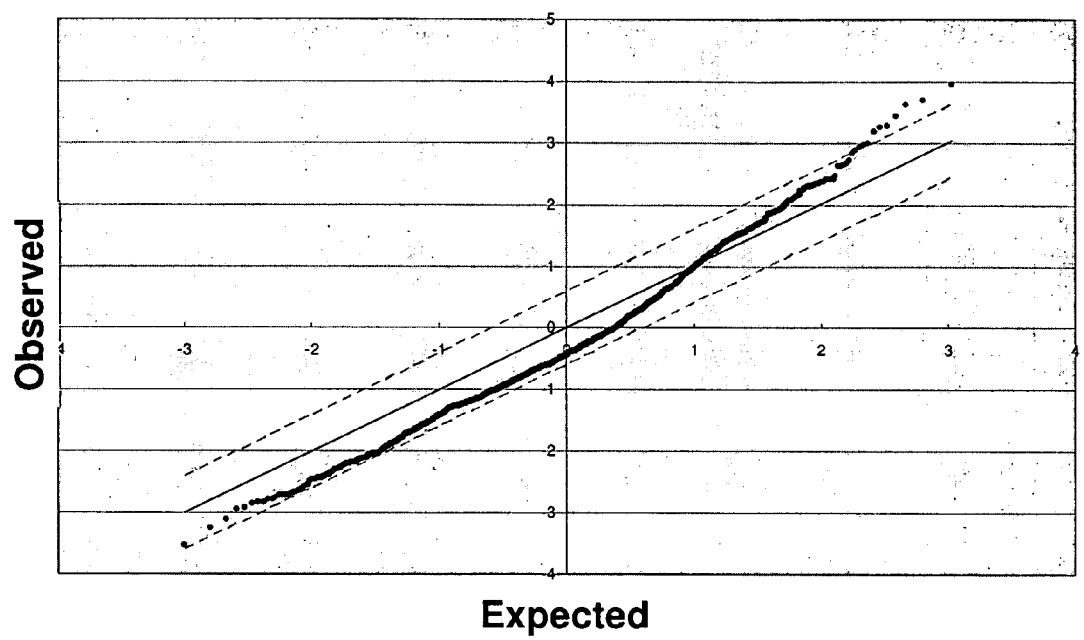
FIG. 1: Identification of protein peaks of interest using SAM methodology SAM analysis was applied to a data set of peak intensities obtained using SELDI-TOF mass spectrometry of plasma samples from subjects with PAD (n=45) or without PAD (n=43). Expected and observed values of each protein peak are plotted. Most peaks fall within a range that is within the expected variation of the normal subjects. Among 1619 peaks, 11 peaks in the PAD group have intensities which fall outside of expected variation in the control group.

A "biomarker" as used herein generally refers to an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median level of the biomarker in a first phenotypic status relative to a second phenotypic status is calculated to represent statistically significant differences. Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest. As such, biomarkers can find use as markers for, for example, disease (diagnostics), therapeutic effectiveness of a drug (theranostics), and of drug toxicity.

"Polypeptide", "protein", and "peptide" used interchangeably herein, refer to a polymeric form of amino acids of any length. In the context of a B2M polypeptide and/or a C reactive protein (CRP) as may be present in a biological sample obtained from a subject (e.g., a human subject), polypeptide and peptide in this context refers to any naturally-occurring form of B2M and of CRP, particularly those detectable by an assay method described herein.

The term "antibody" is meant to include any of a variety of forms of antibodies that specifically bind an antigen of interest, including complete antibodies, fragments thereof (e.g., F(ab')2, Fab, etc.), modified antibodies produced therefrom (e.g., antibodies modified through chemical, biochemical, or recombinant DNA methodologies), single chain antibodies, and the like, with the proviso that the antibody fragments and modified antibodies retain antigen binding characteristics sufficient to facilitate specific detection of an antigen of interest (e.g., B2m or CRP) in an immunoassay.

The term "fusion protein" (also referred to herein as "chimeric protein" or "chimeric polypeptide") includes, but is not limited to, fusions of a first protein with a heterologous amino acid sequence, fusions with heterologous and homologous leader sequences, with or without N-terminal methionine residues; immunologically tagged proteins; and the like.

The term "heterologous" as used in the context of, for example, "heterologous amino acid sequences" or "heterologous nucleic acid sequences", is meant to indicate that a first biological molecule (e.g., polymer) is joined to a second biological molecule (e.g., a polymer) with which it is not normally joined (e.g., covalently bound) in nature. For example, a heterologous amino acid sequence refers to the joining of a first amino acid sequence to a second amino acid sequence with which it is not normally found in nature, and a heterologous nucleic acid sequence refers to the joining of a first nucleic acid sequence to a second nucleic acid sequence with which it is not normally found in nature.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

As used throughout, "modulation" is meant to refer to an increase or a decrease in the indicated phenomenon (e.g., modulation of a level of a biomarker activity encompasses an increase in a biomarker level and a decrease in a biomarker level).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines, simians, humans, felines, canines, equines, bovines, mammalian farm animals, mammalian sport animals, and mammalian pets. Human subjects are of particular interest.

"Biological sample" as used herein refers to a sample obtained from blood of a subject for analysis of B2M and/or CRP levels, and includes a clinical sample, as well as samples that have been stored (with the proviso that storage under conditions to avoid degradation of B2M and CRP). Exemplary biological samples of blood include peripheral blood or samples derived from peripheral blood. In some cases, the blood will have been enriched for a protein fraction containing B2M and/or CRP.

A "blood sample" is a sample which is derived from blood, usually peripheral (or circulating) blood. A blood sample may be, for example, whole blood, plasma or serum.

The phrases "specifically binds", "specifically immunologically cross reactive with," or "specifically immunoreactive with" when referring to a protein or a binding partner that binds a protein (e.g., an antibody), refers to a binding reaction between a protein and a binding partner (e.g., antibody) which is determinative of the presence of the protein in the presence of a heterogeneous population of proteins and other biologics. Thus, under designated conditions, a specified binding partner (e.g., antibody) binds preferentially to a particular protein and does not bind in a significant amount to other proteins present in the sample. A binding partner (e.g., an antibody) that specifically binds to a protein has an association constant of at least $10^3 M^{-1}$ or $10^4 M^{-1}$, sometimes $10^5 M^{-1}$ or $10^6 M^{-1}$, in other instances at least $10^6 M^{-1}$ or $10^7 M^{-1}$, or at least $10^8 M^{-1}$ to $10^9 M^{-1}$, or at least $10^{10} M^{-1}$ to $10^{11} M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

The term "isolated," "purified" or "substantially pure" means an object species (e.g., a protein of interest) is the predominant macromolecular species present (i.e., on a molar basis it is more abundant than any other individual species in the composition), where the object species can comprise at least about 50 percent (on a molar basis) of all macromolecular species present, and can be more than 80 to 90 percent of all macromolecular species present in a composition, and may be purified to essential homogeneity (i.e., contaminant species cannot be detected in the composition by conventional detection methods) wherein the composition consists essentially of a single macromolecular species.

As used herein, the terms "determining", "assessing", "assaying", "measuring" and "detecting" refer to both quantitative and qualitative determinations and as such, the term "determining" is used interchangeably herein with "assaying," "measuring," and the like. Where a quantitative determination is intended, the phrase "determining an amount" of an analyte and the like is used. Where either a qualitative or quantitative determination is intended, the phrase "determining a level" of an analyte or "detecting" an analyte is used.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a biomarker" includes a plurality of such biomarkers and reference to "the sample" includes reference to one or more samples and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Moreover any positively recited element of the disclosure provides basis for a negative limitation to exclude that element from the claims. "Consisting essentially of" as may be used in a claim directed to detecting levels of biomarker(s) is meant to indicate that the claimed method involves detection of the recited biomarkers, but excludes detection of biomarkers that would materially affect the basic and novel characteristic of the claimed method, and thus excludes detection of other biomarkers known to be associated with diagnosis of PAD.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

Embodiments of the present invention relate to use of β-2-microglobulin (B2M or β2M) and C-reactive protein (CRP) levels as biomarkers of peripheral artery disease and/or atherosclerosis.

BETA-2-Microglobulin (B2M OR β2M)

B2M is a component of MHC class I molecules, which are present on almost all cells of the body (except red blood cells). Human B2M is an about 99 amino acid protein derived from a 119 amino acid precursor (see, e.g., GI:1793 18; SwissProt Accession No. P61769). B2M has a molecular weight of about 11.7 KDa (predicted mass: 11,729.17 Da).

Antibodies that specifically bind B2M can be generated using methods known in the art. In addition, antibodies that specifically bind B2M are available from commercial sources. Examples of commercially available anit-B2M antibodies include, without limitation, antibodies available from, e.g., Abcam (catalog AB759) (Cambridge, Mass.).

C-Reactive Protein (CRP)

C-reactive protein (CRP) is a homopentameric oligoprotein composed of monomeric subunits that are each about 21 kD. The human CRP molecule has a relative molecular weight of about 115 kDa (115,135 Da), and is composed of five identical non-glycosylated polypeptide subunits, each having a relative molecular weight of about 23 kDa (23,027 Da), and each containing 206 amino acid residues. (Hirschfield and Pepys Q J Med 2003; 96: 793-807). The form of CRP detected in the assays of the present disclosure is usually the pentameric form, particularly where the assay detects CRP based on molecular weight.

CRP preferentially binds to phosphorylcholine, a common constituent of microbial membranes. The interaction of CRP with phosphorylcholine promotes agglutination and opsonization of bacteria, as well as activation of the complement cascade, all of which are involved in bacterial clearance. CRP can also interact with DNA and histones. The normal plasma concentration of CRP is less than about 3 μg/ml (30 nM) in 90% of the healthy population, and less than about 10 μg/ml (100 nM) in 99% of healthy individuals. It will be appreciated that normal values may exhibit variation in accordance with certain population characteristics such as race, ethnicity, gender, and the like.

Antibodies that specifically bind CRP can be generated using methods known in the art. In addition, antibodies that specifically bind CRP, including monoclonal anti-CRP antibodies, are available from commercial sources. Examples of commercially available anti-CRP antibodies include, without limitation, antibodies available from, e.g., Abcam (catalog AB8280) (Cambridge, Mass.).

B2M and CRP As Biomarkers

B2M and CRP polypeptides can be detected in any form that may be found in a biological sample obtained from a subject, or in any form that may result from manipulation of the biological sample (e.g., as a result of sample processing). Modified forms of B2M and/or CRP can include modified proteins that are a product of allelic variants, splice variants, post-translational modification (e.g., glycosylation, proteolytic cleavage (e.g., fragments of a parent protein), glycosylation, phosphorylation, lipidation, oxidation, methylation, cysteinylation, sulphonation, acetylation, and the like), oligomerization, de-oligomerization (to separate monomers from a multimeric form of the protein), denaturation, and the like.

The assays described herein can be designed to detect all forms or particular forms of either B2M or CRP. Where desired, differentiation between different forms of the same protein can be accomplished by use of detection methods dependent upon physical characteristics that differ between the forms, e.g., different molecular weight, different molecular size, presence/absence of different epitopes, and the like.

Methods for Detection of B2M and CRP

Detection of B2M and CRP can be accomplished by any suitable method. Exemplary detection methods include immunodetection methods, optical methods, electrochemical methods (voltametry and amperometry techniques), atomic force microscopy, and radio frequency methods, e.g., multipolar resonance spectroscopy. In general, it will be understood that it is normally desirable that when assessing a subject's PAD status, B2M and CRP are detected using the same category of detection method.

Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Biochips find use in exemplary methods for detection of B2M and CRP in a sample. A biochip generally comprises a solid substrate having a substantially planar surface, to which a capture reagent (e.g., an adsorbent or affinity reagent) is attached. Frequently, the surface of a biochip comprises a plurality of addressable locations having bound capture reagent bound. The biochip may also include bound capture reagent that serves as a control (e.g., having a bound B2M or CRP)

Protein biochips are biochips adapted for the capture of polypeptides. Many protein biochips are described in the art. These include, for example, protein biochips produced by Ciphergen Biosystems, Inc. (Fremont, Calif.), Zyomyx (Hayward, Calif.), Invitrogen (Carlsbad, Calif.), Biacore (Uppsala, Sweden) and Procognia (Berkshire, UK). Examples of such protein biochips are described in the following patents or published patent applications: U.S. Pat. No. 6,225,047 (Hutchens &Yip); U.S. Pat. No. 6,537,749 (Kuimelis and Wagner); U.S. Pat. No. 6,329,209 (Wagner et al.); PCT International Publication No. WO 00156934 (Englert et al.); PCT International Publication No. WO 031048768 (Boutell et al.) and U.S. Pat. No. 5,242,828 (Bergstrom et al.).

Detection of B2M and CRP can be conducted in the same or different blood samples, the same or separate assays, and may be conducted in the same or different reaction mixture. Where B2M and CRP are assayed in different blood samples, the samples are usually obtained from the subject during the same blood draw or with only a relative short time intervening so as to avoid an incorrect result due to passage of time. Where B2M and CRP are detected in separate assays, the samples assayed are can be derived from the same or different blood samples obtained from the subject to be tested. Where B2M and CRP are assayed in the same reaction mixture in an immunoassay, detection of B2M and CRP in the sample can be accomplished using, for example, antibodies having different, detectably distinct labels so that one can distinguish between detection of specific immunocomplexes containing B2M and specific immunocomplexes containing CRP. For example, the primary anti-B2M and anti-CRP antibodies can have different detectable labels (e.g., different optically detectable labels that provide for different excitation and/or emission wavelengths). In another example, the secondary antibody specific for the primary anti-B2M and the secondary antibody specific for the anti-CRP antibody are differently detectably labeled. Other variations of the assays described herein to provide for different assay formats for detection of B2M and CRP will be readily apparent to the ordinarily skilled artisan upon reading the present disclosure.

Exemplary methods for detection of B2M and CRP are described below.

Immunodetection Methods

B2M and CRP can be detected using a variety of immunodetection methods (also referred to herein as immunoassays). In general, immunoassays detect the presence or absence of biomarker levels (including qualitative and quantitative detection) by detecting formation binding of the biomarker to a biospecific capture reagent, such as an anti-biomarker antibody (an antibody that specifically binds the biomarker). Immunoassays suitable for use in the methods disclosed herein include, for example, sandwich immunoassays including ELISA or fluorescence-based immunoassays, other enzyme immunoassays and western blot. Nephelometry is an example of another immunoassay, which is conducted in liquid phase with antibodies in solution.

Antibodies for use in detection of CRP and B2M

Any of a variety of suitable antibodies that specifically find the target of interest (e.g., CRP or B2M) find use in the detection methods disclosed herein. For example, antibodies can be whole antibodies or antibody fragments, such as those produced using biochemical, chemical, or recombinant DNA techniques. For example, antibody fragments, such as Fv, F(ab')2 and Fab may be prepared from the antibodies of the invention by cleavage of the intact protein, e.g. by protease or chemical cleavage or recombinant production. Use of single chain antibodies (see, e.g., Jost et al. (1994) J. Biol. Chem. 269:26267-73) and of chimeric antibodies (see, e.g., Liu et al. (1987) Proc. Natl. Acad. Sci. 84:3439 and (1987) J. Immunol. 139:3521) are also contemplated.

The antibodies used to assays disclosed herein can include polyclonal antibodies, monoclonal antibodies and fragments thereof as described supra. Usually, the antibody is a monoclonal antibody which specifically binds a target antigen (e.g., B2M or CRP). Monoclonal antibodies can be prepared according to established methods (see, e.g., Kohler and Milstein (1975) Nature 256:495; and Harlow and Lane (1988) Antibodies: A Laboratory Manual (C.H.S.P., N.Y.))

Antibodies useful in the methods disclosed herein include antibodies that are modified relative to a naturally-occurring antibody in any of a variety of ways, with the proviso that the modified antibodies retain specific binding to the original target antigen. The ability of such modified antibodies to bind their original antigen with a desired specificity, affinity, and/or avidity can be assessed in in vitro assays (e.g., in ELISA assays, etc.). Such screening is routine and within the level of skill in the relevant art.

Detectably labeled antibodies find use in certain embodiments of the assays disclosed herein. Any of a number of detectable labels can be provided on an antibody to facilitate direct or indirect detection of the detectably labeled antibody. Exemplary detectable labels include radiolabels (such as $^3$H or $^{125}$I), fluorophores, dyes, magnetic beads, chemiluminescers, colloidal particles, and the like. Examples of labels which permit indirect measurement of binding include enzymes where the substrate may provide for a colored or fluorescent product. Additional exemplary detectable labels include covalently bound enzymes capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Further exemplary detectable labels include biotin, which binds with high affinity to avidin or streptavidin; fluorochromes (e.g., phycobiliproteins, e.g. phycoerythrin and allophycocyanins; fluorescein and Texas red), which can be used with a fluorescence activated cell sorter; haptens; and the like. In some embodiments, the detectable label allows for detection of antibody-antigen complex in a plate luminometer. In other embodiments, the antibody can be bound to a particle (e.g., bead), e.g., as may optionally be used to facilitate detection of specific antigen-antibody complexes by nephelometry.

The assays disclosed herein can use anti-B2M and anti-CRP antibodies that are available in the art (or modified versions thereof), or anti-B2M or anti-CRP antibodies can be readily made. Methods for production of an antibody of interest, including recombinant methods, screening methods to identify antibodies having a desired antigen binding specificity, and methods of providing a detectable label, are routine and well known in the art. Antibodies can be produced by methods well known in the art, e.g., by immunizing animals with a desired target antigen (e.g., B2M or CRP). For example, anti-B2M antibodies and methods for detecting B2M using standard assays are described in the art (see, e.g., Hilgert et al. (Folia Biol (Praha)(1984) 30:369-76; U.S. Pat. No. 4,329,152). Exemplary anti-CRP antibodies and immunoassays are described in U.S. Pat. No. 5,272,258 and U.S. Pat. No. 5,500,345. Examples of the use of these antibodies to detect B2M and CRP in PAD patients relative to normal patients are provided herein.

Samples

Any sample suitable for detection of B2M and CRP to provide an assessment of PAD status in a subject can be used in the assays disclosed herein. In general, the sample is a blood sample obtained from a subject having, suspected of having, or at risk for PAD. "Biological sample" as used herein refers to a sample obtained from a subject for analysis of B2M and/or CRP levels, usually a blood sample. Biological samples includes a clinical sample, and also includes samples that have been processed, stored, or both (with the proviso that processing and storage under conditions to avoid degradation of B2M and CRP). "Blood sample" refers to a biological sample which is derived from blood, usually peripheral (or circulating) blood. A blood sample may be, for example, whole blood, plasma or serum, and may be optionally treated to enrich for a protein fraction containing B2M and/or CRP.

Immunoassays

The immunoassays can be conducted in a variety of different formats, and generally involve the detection of binding between an anti-biomarker antibody (e.g., an anti-B2M or anti-CRP antibody) and its target biomarker antigen (e.g., B2M or CRP, respectively) in a biological sample obtained for a patient. Immunoassays can be conducted in any of a variety of formats, and may be performed either qualitatively or quantitatively. In general, the assay will measure the reactivity between an anti-biomarker antibody and a patient sample.

For example, the assay can be conducted as a sandwich type assay. A sandwich assay is performed by first immobilizing either proteins from the test sample, or anti-biomarker antibodies, on an surface of an insoluble support. Binding to the support may be accomplished by any suitable means, depending upon the nature of the surface, either directly or indirectly and either covalently or non-covalently. The particular manner of binding is not crucial so long as it is compatible with the reagents and overall detection methods. Where the anti-biomarker antibodies are bound to the support, It may be desirable to bind the anti-B2M antibodies and the anti-CRP antibodies to discrete and separate locations on the support so that the presence of absence of antigen-antibody complexes at the different locations can be correlated with the presence or absence of B2M or CRP in the sample.

The insoluble supports can be of any suitable material which is readily separated from soluble material, and which is otherwise compatible with the overall method of detecting B2M and CRP in a sample. The surface of such supports may be solid or porous and of any convenient shape. Examples of suitable insoluble supports to which the receptor is bound include beads, e.g. magnetic beads, latex particles, membranes and microtiter well surfaces.

Before adding patient samples or fractions thereof, it may be desirable to block non-specific binding sites on the insoluble support, i.e. those not occupied by polypeptide or antibody. Exemplary blocking agents include non-interfering proteins such as bovine serum albumin, casein, gelatin, and the like. Alternatively, several detergents at non-interfering concentrations, such as TWEEN, NP40, TX100, and the like may be used.

Samples, fractions or aliquots thereof can be added to separately assayable supports (for example, separate wells of a microtiter plate) or supports with discrete, separately assayable locations, e.g., to which anti-B2M antibodies or anti-CRP antibodies are bound. The assay can include a series of standards, containing known concentrations of B2M and/or CRP, so as to provide an internal positive and/or negative control. Where desired, multiple samples and standards can be assays so that mean values can be obtained for each.

The support having bound test sample (or bound anti-B2M and/or anti-CRP antibodies) is incubated with the anti-biomarker antibody(ies) (or with test sample, where the support has bound anti-biomarker antibodies) for a time sufficient for formation of specific antigen-antibody complexes. After incubation, the insoluble support is generally washed of non-bound components. For example, the support can be washed with a dilute non-ionic detergent medium at an appropriate pH, generally 7-8. Washing can be repeated as desired so as to provide for removal of non-specifically bound proteins to an acceptable level.

After washing, the presence or absence of specific antigen-antibody complexes (also referred to as "specific immuno-complexes" or "specific immune complexes") is detected. Where the test sample is bound to the support, the presence or absence of specific immunocomplexes can be detected directly, e.g., by virtue of a detectable label on the anti-biomarker antibody. Where the antibody is not detectably labeled and the assay involves immobilized test sample, specific immunocomplexes can be detected by contacting the sample with a solution containing a detection reagent, e.g., an antibody-specific detection reagent to detect antibody bound to immobilized test protein (e.g., a secondary antibody (i.e., an anti-antibody)). The detection reagent may be any compound which binds antibodies with sufficient specificity such that the bound antibody is distinguished from other components present. For example, detection reagents can be antibodies specific for the anti-biomarker antibody, and may be either monoclonal or polyclonal sera, e.g. goat anti-mouse antibody, rabbit anti-mouse antibody, etc.

The detection reagent can be labeled to facilitate direct, or indirect detection of binding. Examples of labels which permit direct measurement of the detection reagent include light-detectable labels, radiolabels (such as $^3$H or $^{125}$I), fluorescers, dyes, beads, chemiluminescers, colloidal particles, and the like. Examples of labels which permit indirect measurement of binding include enzymes where the substrate may provide for a colored or fluorescent product. In one embodiment, the detection reagent is an antibody labeled with a covalently bound enzyme capable of providing a detectable product signal after addition of suitable substrate. Examples of suitable enzymes for use in conjugates include horseradish peroxidase, alkaline phosphatase, maleate dehydrogenase and the like. Where not commercially available, such antibody-enzyme conjugates are readily produced by techniques known to those skilled in the art.

Alternatively, the detection reagent may be unlabeled. In this case, a labeled second detection reagent specific for the first detection reagent is used, where the second detection reagent can be labeled in any of the above manners. Such compounds can be selected such that multiple compounds bind each molecule of bound second receptor. Examples of second detection reagent/first detection reagent-specific pairs include antibody/anti-antibody and avidin (or streptavidin)/biotin. Since the resultant signal is thus amplified, this technique may be advantageous where only a small amount of biomarker may be present, or where the background measurement (e.g., non-specific binding) is unacceptably high. An example is the use of a labeled antibody specific to the first detection reagent.

Where the anti-biomarker antibody is bound to the support, formation of specific immune complexes can be accomplished using an antibody to detect the presence or absence of specific biomarker-antibody immunocomplexes. The detection antibody can be the same or different from the bound antibody, with the proviso that the epitopes to which the detection antibody binds are available when the biomarker is in the immunocomplex with the bound anti-biomarker antibody. As described above, the detection antibody can be labeled or unlabeled, and the formation of specific immunocomplexes of bound anti-biomarker antibody-biomarker-detection antibody detected directly (e.g., by virtue of the detectable label on the detection antibody) or indirectly (e.g., by use of a third reagent that detects the detection antibody in the immunocomplex).

After incubation with the reagents for a time sufficient to allow binding of specific immunocomplexes, the insoluble support is generally again washed free of non-specifically bound detection reagent(s). After non-specifically bound material has been cleared, the signal produced by the bound conjugate is detected by any suitable means compatible with the assay format. For example, where an enzyme conjugate is used, an appropriate enzyme substrate is provided so a detectable product is formed. For example, where the detection involves peroxidase in an enzyme conjugate, the substrate is usually a combination of hydrogen peroxide and O-phenylenediamine which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art. For the product of the substrate O-phenylenediamine for example, light absorbance at 490-495 nm is conveniently measured with a spectrophotometer.

The presence or absence anti-biomarker antibody binding may be determined by various methods that are compatible with the detectable label used, e.g., microscopy, radiography, scintillation counting, etc. Generally a level of specific antibody-biomarker immunocomplexes is compared to a level of one or more control samples, and the results evaluated to facilitate a diagnosis. Control samples can be run in parallel to provide comparison levels, or the levels of specific immunocomplexes in a control level provided as standard values for purposes of comparison.

The immunoassay described here can take a variety of forms. Exemplary formats include, but are not limited to, competitive binding assays, in which formation of immunocomplexes is performed in the presence of different amounts of a competitor protein (e.g., B2M or CRP) which competes for binding to the anti-biomarker antibody. The competitor molecule can be labeled and detected as previously described, where a decrease in competitor binding will be proportional to the level of biomarker present in the sample.

The detection assays can be carried out in solution. For example, the anti-B2M and/or anti-CRP antibody can be combined with the test sample, and immune complexes of anti-biomarker antibody and biomarker are detected. One detection method of interest involves nephelometry, in which detection of immunocomplexes is detected as a change in light absorbance. Assays compatible with detection by nephelometry include those using unlabeled anti-biomarker antibodies, which antibodies may be bound to a suitable support, e.g., a particle that can be suspended in solution. Exemplary assays and reagents compatible for use in assays for immunocomplex detection by nephelometry are known in the art, see, e.g., U.S. Pat. No. 4,311,788; U.S. Pat. No. 5,466,611; U.S. Pat. No. 5,166,077, which describe exemplary nephelometric assays and techniques which may be adapted for use in the assays disclosed herein.

Other immunoassays (e.g., Ouchterlony plates or Western blots may be performed on protein gels or protein spots on filters) are known in the art and may find use as diagnostics.

Further guidance regarding the methodology and steps of a variety of antibody assays is provided, for example, in U.S. Pat. No. 4,376,110 to Greene; "Immunometric Assays Using Monoclonal Antibodies," in Antibodies: A Laboratory Manual, Cold Spring Harbor Laboratory, Chap. 14 (1988); Bolton and Hunter, "Radioimmunoassay and Related Methods," in Handbook of Experimental Immunology (D. M. Weir, ed.), Vol. 1, chap. 26, Blackwell Scientific Publications, 1986; Nakamura, et al., "Enzyme Immunoassays: Heterogeneous and Homogenous Systems," in Handbook of Experimental Immunology (D. M. Weir, ed.), Vol. 1, chap. 27, Blackwell Scientific Publications, 1986; and Current Protocols in Immunology, (John E. Coligan, et al., eds), chap. 2, section I, (1991).

Mass Spectrometry Detection Methods

Mass spectrometry-based methods exploit the differences in mass of biomarkers to facilitate detection. Mass spectrometry can be combined with immunoassays, e.g., by first forming specific biomarker-antibody immunocomplexes, and detecting the presence or absence of the specific immunocomplexes by mass spectroscopy. In general, an anti-biomarker antibody is used to capture the biomarker of interest (e.g., B2M or CRP). The anti-biomarker antibody can be bound to a support, such as a bead, a plate, a membrane or a chip. After unbound materials are washed away, the captured biomarkers are detected by mass spectrometry. Examples of mass spectrometers are time-of-flight, magnetic sector, quadmpole filter, ion trap, ion cyclotron resonance, electrostatic sector analyzer and hybrids of these.

Various forms of mass spectrometry are useful for detecting the protein forms. Thus, when reference is made herein to detecting a particular protein or to measuring the amount of a particular protein, such encompasses detecting and measuring the protein with or without resolving various forms of protein. For example, the step of "measuring B2M" or "measuring CRP" includes measuring B2M or measuring CRP by means that do not differentiate between various forms of these proteins (e.g., certain immunoassays) as well as by means that differentiate some forms from other forms or that measure a specific form of the protein. In contrast, when it is desired to measure a particular form or forms of a protein, the particular form (or forms) is specified. For example, "measuring B2M (MI 1.7K)" means measuring B2M M11.7K in a way that distinguishes it from other forms of B2M.

The mass spectrometer can be a laser desorption/ionization (LDI) mass spectrometer. In LDI mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer. The analyis of proteins by LDI can take the form of MALDI or of SELDI.

MALDI

MALDI is a method of laser desorption/ionization used to analyze biomolecules, including proteins. In one MALDI method, the sample is mixed with matrix and deposited directly on a MALDI chip. Where a complex biological sample such as blood is used as in the present assays, it is useful to first fractionate the sample prior to application to the MALDI chip. Accordingly, B2M and CRP can be first captured with biospecific (e.g., an antibody) or chromatographic materials coupled to a solid support such as a resin (e.g., in a spin column). Specific affinity materials that bind B2M or CRp are described above. After purification on the affinity material, the biomarkers are eluted and then detected by MALDI.

SELDI

"Surface Enhanced Laser Desorption and Ionization", or "SELDI," is another mass spectrometric technique which can be adapted for use in the methods disclosed herein. Exemplary SELDI techniques that may be adapted to the present methods are described in, for example, U.S. Pat. No. 5,719,060 and U.S. Pat. No. 6,225,047. SELDI refers to a method of desorption/ionization gas phase ion spectrometry (e.g., mass spectrometry) in which an analyte (here, one or more of B2M and CRP) is captured on the surface of a SELDI mass spectrometry probe.

SELDI also has been referred to as "affinity capture mass spectrometry" or "Surface-Enhanced Affinity Capture" ("SEAC"). This version involves the use of probes that have a material on the probe surface that captures analytes (here, B2M or CRP) through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte, e.g., an anti-CRP antibody or an anti-B2M antibody). The capture reagent is attached to the probe surface by physisorption or chemisorption. In certain embodiments the probes have the capture reagent already attached to the surface. In other embodiments, the probes are pre-activated and include a reactive moiety that is capable of binding the capture reagent, e.g., through a reaction forming a covalent or coordinate covalent bond. Epoxide and acyl-imidizole are useful reactive moieties to covalently bind polypeptide capture reagents such as antibodies or cellular receptors. Nitrilotriacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitrilotriacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents). "Biospecific adsorbent" refers to an adsorbent comprising a biomolecule, e.g., such as an antibody. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to an adsorbent that binds to an analyte with an affinity of at least $10^{-8}$ M.

Protein biochips produced by Ciphergen Biosystems, Inc. comprise surfaces having chromatographic or biospecific adsorbents attached thereto at addressable locations. Ciphergen ProteinChip® arrays include NP20 (hydrophilic); H4 and H50 (hydrophobic); SAX-2, Q-10 and (anion exchange); WCX-2 and CM-10 (cation exchange); IMAC-3, IMAC-30 and IMAC-50 (metal chelate); and PS-10, PS-20 (reactive surface with acyl-imidizole, epoxide) and PG-20 (protein G coupled through acyl-imidizole). Hydrophobic ProteinChip arrays have isopropyl or nonylphenoxy-poly(ethylene glycol)methacrylate functionalities. Anion exchange ProteinChip arrays have quaternary ammonium functionalities. Cation exchange ProteinChip arrays have carboxylate functionalities. Immobilized metal chelate ProteinChip arrays have nitrilotriacetic acid functionalities (IMAC 3 and IMAC 30) or O-methacryloyl-N,N-bis-carboxymethyl tyrosine functionalities (IMAC 50) that adsorb transition metal ions, such as copper, nickel, zinc, and gallium, by chelation. Preactivated ProteinChip arrays have acyl-imidizole or epoxide functional groups that can react with groups on proteins for covalent binding. Such biochips are further described in: U.S. Pat. No. 6,579,719; U.S. Pat. No. 6,897,072; U.S. Pat. No. 6,555,813; US 2003-0032043; WO 03/040700; US 2003-0218130; and U.S. 2005-059086.

In general, a probe with an adsorbent surface is contacted with the sample for a period of time sufficient to allow the biomarker or biomarkers that may be present in the sample to bind to the adsorbent. After an incubation period, the substrate is washed to remove unbound material. Any suitable washing solutions can be used. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

In yet another method, one can capture the biomarkers with a solid-phase bound immunoadsorbent having anti-B2M or anti-CRP antibodies. After washing the adsorbent to remove unbound material, the biomarkers are eluted from the solid phase and detected by applying to a SELDI chip that binds the biomarkers and analyzing by SELDI.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

SEND

Surface-Enhanced Neat Desorption ("SEND") is another laser desorption mass spectrometry method that can be adapted for use in the methods disclosed herein. SEND involves the use of probes comprising energy absorbing molecules that are chemically bound to the probe surface ("SEND probe"). The phrase "energy absorbing molecules" (EAM)

denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyaceto-phenone derivatives. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano-4-methacryloyloxycinnamic acid, acrylate and 3-(tri-ethoxy)silyl propyl methacrylate. In another embodiment, the composition is a co-polymer of α-cyano-4-methacryloyloxycinnamic acid and octadecylmethacrylate ("C18 SEND"). SEND is further described in, for example, U.S. Pat. No. 6,124,137 and WO 03/64594.

SEAC/SEND is a version of laser desorption mass spectrometry in which both a capture reagent and an energy absorbing molecule are attached to the sample presenting surface. SEAC/SEND probes therefore allow the capture of analytes through affinity capture and ionization/desorption without the need to apply external matrix. The C18 SEND biochip is a version of SEAC/SEND, comprising a C18 moiety which functions as a capture reagent, and a CHCA moiety which functions as an energy absorbing moiety.

SEPAR

Another version of LDI is that can be adapted for use in the methods disclosed herein is called Surface-Enhanced Photolabile Attachment and Release ("SEPAR"). SEPAR involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker profile, pursuant to the present invention.

Other Forms of Ionization in Mass Spectrometry

In another method, the biomarkers are detected by LC-MS or LC-LC-MS. This involves resolving the proteins in a sample by one or two passes through liquid chromatography, followed by mass spectrometry analysis, typically electrospray ionization.

Analysis of Mass Spectrometry Data

Analysis of B2M and CRP analytes by time-of-flight mass spectrometry generates a time-of-flight ("TOF") spectrum. The TOF spectrum ultimately analyzed typically does not represent the signal from a single pulse of ionizing energy against a sample, but rather the sum of signals from a number of pulses. This reduces noise and increases dynamic range. This TOF data can then be subjected to data processing. For example, in Ciphergen's PROTEINCHIP® software, data processing typically includes TOF-to-M/Z transformation to generate a mass spectrum, baseline subtraction to eliminate instrument offsets and high frequency noise filtering to reduce high frequency noise.

Data generated by desorption and detection of biomarkers can be analyzed with the use of a programmable digital computer. The computer program analyzes the data to indicate the number of biomarkers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte. Peak selection can be done visually, but software is available, as part of Ciphergen's PROTEINCHIP® software package, that can automate the detection of peaks. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis, to determine whether a biomarker peak or combination of biomarker peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

Exemplary Protocol for SELDI Detection of Biomarkers for Peripheral Artery Disease In one embodiment, detection of the CRP and B2M biomarkers is accomplished as follows. The biological sample to be tested, e.g., serum, is subjected to pre-fractionation before SELDI analysis to simplify analysis and improve sensitivity. Pre-fractionation can be accomplished by, for example, contacting the sample with an anion exchange chromatographic material, such as Q HyperD (BioSepra, SA). The bound materials are then subjected to stepwise pH elution using buffers at pH 9, pH 7, pH 5 and pH 4. Various fractions containing the biomarker are collected.

The sample to be tested is contacted with an affinity capture probe comprising a cation exchange adsorbent (e.g., a CM10 PROTEINCHIP® array (Ciphergen Biosystems, Inc.)) or an IMAC adsorbent (preferably an IMAC30 PROTEINCHIP® array (Ciphergen Biosystems, Inc.)). The probe is washed with a buffer that will retain the biomarker while washing away unbound molecules, and biomarkers are detected by laser desorption/ionization mass spectrometry.

Alternatively, samples may be diluted, with or without denaturing, in the appropriate array binding buffer and bound and washed under conditions optimized for detecting each analyte.

Alternatively, anti-biomarker antibodies are attached to the surface of a probe, such as a pre-activated PS10 or PS20 ProteinChip array (Ciphergen Biosystems, Inc.). These antibodies capture the B2M or CRP from a sample onto the probe surface, and the presence of the biomarkers in specifici immunocomplexes detected by, e.g., laser desorption/ionization mass spectrometry.

Any robot that performs fluidics operations can be used in these assays, for example, those available from Tecan or Hamilton.

Determination of Peripheral Artery Disease (PAD) Status

The B2M and CRP biomarkers can be used in diagnostic tests to assess peripheral artery disease PAD status in a subject, e.g., to diagnose PAD. The phrase "peripheral artery disease status" ("PAD status") includes any distinguishable manifestation of the disease, including non-disease. For example, PAD status includes, without limitation, the presence or absence of disease (e.g., PAD vs. non-PAD), the risk of developing PAD, the stage of the disease, the progression of PAD (e.g., progress of disease or remission of disease over time), and the effectiveness or response to treatment of PAD. Determination of PAD status can also include providing a differential diagnosis between PAD and coronary artery disease (CAD), so as to facilitate a diagnosis of CAD versus PAD, and/or facilitate diagnosis of the presence or absence of PAD in a subject having CAD.

The correlation of the results of tests for B2M and CRP levels with PAD status generally involves applying a classification algorithm to the results from an individual to generate a PAD status. The classification algorithm may be as simple as determining whether or not each of the B2M and CRP levels (e.g., amounts) are above or below a particular cut-off number, also referred to as a "threshold" value. Levels of B2M above the B2M threshold are considered "high" B2M levels; levels of B2M below the B2M threshold are considered "low" B2M levels. Levels of CRP above the CRP threshold are considered "high" CRP levels; levels of CRP below the CRP threshold are considered "low" CRP levels.

In general, the "threshold" value for a biomarker in the context of the present method for assessing PAD status refers a median value of a range of biomarker levels (e.g., amounts) of a selected subject population. Use of a median value for a selected subject population as a threshold value is suitable for evaluating high and low CRP levels and for evaluating high and low B2M values in view of the left skewed distributions of CRP and B2M across a population. Thus a "high" biomarker level is a level of biomarker that is greater than this threshold value; a "low" biomarker level is lower than this threshold value. Stated differently, a threshold value is a median value such that a test value above, usually significantly above, the median value is classified as "high" and a test value below, usually significantly below, the median value is classified as "low". In one example, a threshold value for CRP is about 1.6 mg/dl and a threshold value for B2M is about 1.7 mg/dl.

It may also be suitable to divide values of biomarker levels of a subject population into more finely divided groups, e.g., into quartiles or quintiles. For example, a median biomarker level can be used to define a cut-off value between a upper middle quartile values and lower middle quartile values, with the upper quartile and upper middle quartile representing roughly equal numbers of biomarker values from the subject population that are above the median, and the lower middle quartile and lower quartile representing roughly equal numbers of biomarker values below the median value. Evaluation of PAD risk can be assessed by, for example, assigning a subject to a quartile/quintile according to assessed biomarkers levels, where the quartile/quintile associated with the highest CRP and B2M levels representing the highest risk of PAD.

According to the present disclosure, if a subject exhibits a low CRP level and a low B2M level, the PAD status of the subject is at low to no risk of PAD, and may facilitate a diagnosis of "non-PAD". If a subject exhibits a high CRP level and a low B2M level, the PAD status of the subject is low risk of PAD (and which may facilitate a diagnosis of non-PAD), but with increased risk of PAD relative to low CRP/low B2M. If a subject exhibits a low CRP level and a high B2M level, the PAD status of the subject is elevated risk of PAD, which may be described as borderline PAD, with further elevated risk of PAD relative to low CRP/low B2M. If a subject exhibits both a high CRP level and a high B2M level, the subject is diagnosed as high risk of PAD, and may serve as the basis for a differential diagnosis of PAD. "Risk" of PAD as assessed by CRP and B2M levels generally refers to a probability that the patient being evaluated has or will develop PAD compared to a probability that another individual of the same age and gender has or will develop PAD.

The threshold value for CRP levels and for B2M levels can be readily determined, and may vary with patient factors such as age, body mass index (BMI), renal function (e.g., as assessed by glomerular filtration rate (GFR)), smoker status (e.g., smoker vs. non-smoker, moderate vs. excessive smoking, and the like), gender, and the like.

The classification algorithm may be a linear regression formula or may be the product of any of a number of learning algorithms described herein. In the case of complex classification algorithms, it may be necessary to perform the algorithm on the data, thereby determining the classification, using a computer, e.g., a programmable digital computer. In either case, one can then record the status on tangible medium, for example, in computer-readable format such as a memory drive or disk or simply printed on paper. The result also could be reported on a computer screen.

Accordingly, the present disclosure provides a system for classifying PAD status in a subject. The system comprises an input device for entering a value reflecting a detected CRP level and a value reflecting a detected B2M level, wherein CRP and B2M values are obtained from assaying one or more samples from a patient. The input device is operatively linked to a computer having a computer readable medium on which is disposed an executable program that executes program to apply a classification algorithm to the CRP and B2M values entered through the input device, so as to provide for a classification of the PAD status of the patient based on the entered values. The computer is operatively linked to a display on which the results of application of the classification algorithm can be displayed to the user (e.g., in the form of a report). The input device, computer, and display can be provided in a unitary system (e.g., as in a handheld device). Alternatively, one or more of the input device, computer, and display can be at locations remote relative to one another. For example the input device and display can be remote to the computer having the computer readable medium containing the executable program (and can be linked by, for example, the internet)). In another example, the input device is remote to both the computer and the display, e.g., so as to provide for analysis of the values and display of results at a site remote to the site of input by a user).

Generation of PAD Classification Algorithm

Generation of PAD classification algorithms can be accomplished according to routine methods available in the art. For example, data derived from immunoassays or from the spectra (e.g., mass spectra or TOF spectra) that are generated using samples having a known CRP or B2M classification ("known samples") can then be used to "train" a classification model. A "known sample" is a sample that has been pre-classified. The data that are derived from the spectra and are used to form the classification model can be referred to as a "training data set." Once trained, the classification model can recognize patterns in data derived from assays generated using unknown samples. The classification model can then be used to classify the unknown samples into classes. This can be useful, for example, in predicting whether or not a particular biological sample is associated with a certain biological condition (e.g., PAD vs. non-PAD).

The training data set that is used to form the classification model may comprise raw data or pre-processed data. In some embodiments, raw data can be obtained directly from immunoassay, TOF spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, 22(1): (2000), incorporated herein by reference for disclosure.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART classification and regression trees), artificial neural networks such as back propagation networks, discriminant analyses (e.g., Bayesian classifier or Fischer analysis), logistic classifiers, and support vector classifiers (support vector machines).

An exemplary supervised classification method is a recursive partitioning process. Recursive partitioning processes use recursive partitioning trees to classify data derived from unknown samples. Further details about recursive partitioning processes are provided in US 2002/0138208.

In other embodiments, the classification models can be generated using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms that can be used or adapted for use in classifying biological information are described in, for example, WO 01131580; US 2002/0193950; US 2003/0004402; and US 2003/0055615.

The classification models can be formed on and used on any suitable digital computer. Suitable digital computers include micro, mini, or large computers using any standard or specialized operating system, such as a Unix-, WINDOWS®- or LINUX®-based operating system. The digital computer that is used may be physically separate from the assay device (e.g., the mass spectrometer) that is used to create the data of interest, or it may be coupled to the device.

The training data set and the classification models can be embodied by computer code that is executed or used by a digital computer. The computer code can be stored on any suitable computer readable media including optical or magnetic disks, sticks, tapes, etc., and can be written in any suitable computer programming language including C, C++, visual basic, and the like.

The learning algorithms described above are useful for developing classification algorithms (e.g., for specific patient populations, which may be characterized according to one or more patient-based factors such as, for example, race, ethnicity, age, weight, BMI, cardiovascular disease risk factors, and the like). The classification algorithms, in turn, form the basis for diagnostic tests by providing diagnostic threshold values (e.g., cut-off points) for CRP and B2M in different patient populations where such prove useful, e.g., to reduce false positives, reduce false negatives, and the like.

PAD Status

Determining peripheral artery disease status typically involves classifying an individual into one of two or more groups (statuses) based on the results of the diagnostic test. The diagnostic tests described herein can be used to classify between a number of different states. The phrase "PAD status", as discussed above, includes distinguishing PAD from non-PAD (e.g., normal in that the subject is diagnosed as not having PAD, although a disease other than PAD may be present), and distinguishing PAD from CAD.

Based on this status, further procedures may be indicated, including additional diagnostic tests or therapeutic procedures or regimens. Exemplary applications of the assessment of PAD status of a subject based on B2M and CRP levels are described below.

Diagnosis of PAD

B2M and CRP levels and their correlation with PAD status can be used to facilitate diagnosis of PAD in a subject (e.g., the presence or absence of PAD). The presence or absence of PAD is determined by detecting B2M and CRP levels, and then either submitting these levels to a classification algorithm or comparing them with a reference amount and/or pattern of B2M and CRP levels associated with a particular risk level of PAD.

Risk of Developing PAD

In another embodiment, the disclosure provides methods for determining the risk of developing PAD in a subject (e.g., a low-risk of PAD or high risk of PAD). B2M and CRP levels are assessed in a subject, and the levels compared to B2M and CRP levels or patterns characteristic of various risk states, e.g., high, medium or low. The risk of developing PAD can be determined by assessing CRP and B2M levels, and then either submitting this information to a classification algorithm or comparing with a reference level and/or CRP/B2M characteristics of a particular risk level. In general, low CRP/low B2M indicates low risk of PAD; high CRP/low B2M indicates an elevated, but low to medium risk of PAD; low CRP/high B2M indicates an elevated, medium risk of PAD; and high CRP/high B2M indicates a high risk of PAD (including the presence of PAD in the subject). CRP and B2M levels can also be assessed in heredity studies to determine if the subject is at risk for developing PAD.

Stage of PAD

The disclosure also provides methods for classifying the stage of PAD in a subject, i.e., for classifying the severity of PAD in a subject. Increasing severity of PAD can be classified according to levels and/or patterns of CRP and B2M levels characteristic of PAD severity. The stage of PAD can be determined by detecting CRP and B2M levels, then either submitting them to a classification algorithm or comparing them with a reference amount and/or pattern of CRP and B2M associated with the particular stage of PAD. For example, by assessing CRP and B2M levels, one can classify a subject having PAD as being non-PAD, early stage PAD, or severe (late-stage) PAD.

PAD Progression

CRP and B2M levels can also be assessed in the context of assessing the course of PAD. "Disease course" or "progression" refers to changes in disease status over time, including disease progression (worsening) and disease regression (improvement). Over time, the levels (e.g., amounts or relative amounts) (e.g., the pattern) of CRP and B2M can change, with trends toward or maintenance of both high CRP and high B2M indicative of PAD progression, and trends toward or maintenance of both low CRP and low B2M indicative of PAD regression. Changes in only one of CRP level and B2M level can be indicative of PAD progression or regression. For example, and increase in CRP without an increase in B2M indicates a trend toward PAD (PAD progression), with an increase in B2M without an increase in CRP more strongly indicative of a trend toward PAD (PAD progression). Thus, in general, increases or decreases in CRP and B2M levels over time are indicative of trends toward diseased or non-diseased states with respect to PAD, and can be used to monitor the course of the disease. Accordingly, the disclosure includes methods involving assessing CRP and B2M levels in a subject for at least two different time points, e.g., a first time and a second time, and determining the presence or absence of a change in one or both of CRP and B2M levels at the second time compared to the first time. Comparisions of CRP and B2M levels over time can thus facilitate assessment of PAD course.

Response to PAD Therapy

CRP and B2M levels can also be used to assess response to PAD therapy, e.g., to qualify PAD status before and during, as well as after, administration of PAD therapy. In a related embodiment, PAD therapy can be adjusted (e.g., continue therapy, discontinue therapy, adjust dose or type of therapy, etc.) as may be indicated by CRP and B2M levels. Such management includes the actions of the physician or clinician subsequent to determining PAD status. For example, following a diagnosis of PAD, a certain regimen of PAD treatment may be administered. A suitable regimen of PAD treatment may include, without limitation, a supervised exercise program; control of blood pressure, sugar intake, and/or lipid levels; cessation of smoking, including any necessary counseling and nicotine replacement; and drug therapies including the administration of aspirin (with or without dipyridamole), clopidogrel, cilostazol, and/or pentoxifylline. Alternatively, a diagnosis of PAD might be followed by further testing to determine whether a patient is suffering from a specific form of PAD. Furthermore, a diagnosis of PAD may suggest examination of the subject for other conditions that often present with PAD, such as coronary artery disease.

Determining Therapeutic Efficacy Of PAD Therapy

The correlation of CRP and B2M levels with APD can also be exploited to assess therapeutic efficacy of a pharmaceutical drug. These methods are useful in performing clinical trials of a candidate drug for PAD, as well as monitoring the progress of a patient on the drug. Therapy or clinical trials generally involve administering the drug in a particular regimen, and may involve a single dose of the drug or multiple doses of the drug over time. The doctor or clinical researcher monitors the effect of the drug on the patient or subject over the course of administration. If the drug has a beneficial impact on PAD, the levels of CRP and B2M shift toward a non-PAD profile (i.e., toward low CRP/low B2M). CRP and B2M levels, and thus course of PAD and response to therapy, can be followed during the course of treatment. CRP and B2M levels can also be assessed so as to select subjects appropriate for inclusion (or exclusion) in a clinical trial, where desired. For example, CRP and B2M levels can be assessed to determine inclusion or exclusion of a subject in a clinical trial to assess efficacy of a candidate PAD therapy.

In such embodiments, the CRP and B2M levels are assessed in a subject receiving drug therapy, and the CRP and B2M levels correlated with the disease status of the subject. One embodiment of this method involves determining the levels of CRP and B2M for at least two different time points during a course of therapy, e.g., a first time and a second time, and comparing the change in levels of CRP and B2M, if any. For example, CRP and B2M levels can be assessed before and after candidate drug administration or at two different time points during candidate drug administration. The effect of therapy is determined based on these comparisons. If a treatment is effective, then the CRP and B2M levels will trend away from a positive PAD status and toward normal (non-PAD), while if treatment is ineffective, the CRP and B2M levels will trend or be maintained at those indicative of PAD.

Reporting PAD Status

Assay results and/or diagnoses can be communicated to a health care professional (e.g., physician), lab technician, or patient, in a variety of ways. For example, in certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are communicated.

In one embodiment, a diagnosis based on CRP and B2M levels in a test subject is communicated to the subject by the subject's treating physician, by email (or other wise over the internet), or by phone. A computer may be used to communicate the diagnosis (e.g., by email or phone). In certain embodiments, the message containing results of a PAD diagnostic test may be generated and delivered to the subject using a combination of computer hardware and software which will be familiar to those of ordinary skill in the telecommunication arts. An exemplary healthcare-oriented communications system is described in U.S. Pat. No. 6,283,761; however, the present invention is not limited to methods which utilize this particular communications system. In certain embodiments, all or some of the method steps, including the assaying of samples, diagnosing of diseases, and communicating of assay results or diagnoses, may be carried out in diverse jurisdictions, including those outside the U.S.

Use of B2M and CRP in Screening Assays

CRP and B2M levels can also be assessed in screening assays to identify candidate agents that affect CRP and B2M levels, e.g., decrease both CRP and B2M levels, and thus can find use in treatment and/or prevention of PAD. Compounds suitable for therapeutic testing may be screened initially by identifying compounds which interact with at least one of CRP and B2M, and/or which affect CRP and B2M levels (e.g., expression levels) in in vitro assays (e.g., cell-based assays) or in an animal model.

For example, assays can be conducted by administering a candidate agent to an animal model of PAD, such as a model of hindlimb ischemia, to mimic peripheral arterial disease in humans. Assays to assess the effect of a candidate agent on B2M and/or CRP levels can be conducted as described herein. For example after one or more different time points after administration, B2M and/or CRP levels, usually both B2M and CRP levels, the presence or absence of an affect can be assesd by evaluating production of B2M and/or CRP, e.g., by assessing an effect of gene transcription and/or protein production) in the presence of the agent relative to in the absence of the agent, wherein the presence or absence of an affect on B2M and/or CRP production is indicative of the presence or absence of activity of the candidate agent in modulating B2M and/or CRP. The effect of a candidate agent upon B2M and CRP may be conducted in parallel (e.g., at the same time in the same or different samples), or at different times.

Kits

Kits to facilitate assessment of CRP and B2M levels, and thus facilitate assessment of PAD status of a subject, are also provided by the present disclosure. In one embodiment, the kit comprises a solid support, such as a chip, a microtiter plate or a bead or resin having a capture reagent attached to a support surface, wherein the capture reagent specifically binds CRP or B2M. The kits can include at least two types of supports—one for specific detection of CRP and one for specific detection of B2M. Alternatively or in addition, the kits can include supports having capture reagents for both CRP and B2M, where the supports either have the CRP and B2M capture reagents are separately addressable, separately detectable regions on the support, and/or which are useful with detection reagents that provide for different detectable signals for detection of CRP and for detection of B2M that may be captured on the support. Exemplary kits include those that contain immunoassay reagents (e.g., supports having bound anti-CRP and/or anti-B2M antibodies), mass spectrometry probes (e.g., suitable for use in SELDI assays), and the like. The supports and detection reagents can be provide in separate containers as appropriate.

Kits can further optionally include washing solution(s) or instructions for making a washing solution, in which the combination of the capture reagent and the washing solution allows capture of the biomarkers on the solid support for subsequent detection by, e.g., immunodetection, mass spectrometry, etc. The kit may include more than type of adsorbent, each present on a different solid support. Kits can also include one or more containers with CRP and B2M samples, which can be used as standard(s) for calibration as may be desired.

Kits can further comprise instructions for suitable operational parameters in the form of a label or separate insert. For example, the instructions may inform a consumer about how to collect the sample, how to wash the probe or the particular biomarkers to be detected.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec. second(s); min, minute(s); h or hr. hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Methods and Materials

The following methods and materials were used in the Examples set out below.

Patient Population

A total of 371 subjects were investigated in three serial studies: a discovery study (n=88); followed by confirmation (n=40); and validation (n=237) studies. The subjects for the discovery and confirmation studies were recruited as part of the NO-PAIN Study. (Oka et al. *Vasc Med.* 2005; 10(4):265-274). In the NO PAIN study, subjects were recruited by advertisements targeting individuals with leg pain that limited the ability to walk. (Oka et al, supra). Respondents were screened by a structured and standardized telephone interview and eligible subjects were invited for further assessment. After informed consent, subjects underwent a physical examination, measurement of ankle and brachial systolic pressures, and treadmill testing using the Skinner-Gardner protocol. (Hiatt et al. *Vascular Clinical Trialists. Circulation.* 1995; 92(3):614-621).

Subjects for the validation study were derived from the ongoing GenePAD study. In the GenePAD study, subjects were recruited from individuals undergoing coronary angiography at Stanford University or Mount Sinai Medical Centers. The PAD status of these individuals was not known to the investigators at the time of recruitment. Ankle-brachial index (ABI) was determined prior to a comprehensive clinical characterization which included questionnaires to elicit demographics, ethnicity, quality of life, functional capacity; venipuncture for plasma, serum and genomic DNA; and coronary angiography. Patients with PAD had an ABI at rest of <0-90, or in those with non-compressible ankle arteries, a toe-brachial index of <0-60. Glomerular filtration rate (GFR) was estimated by the Modification of Diet in Renal Disease Study (MDRD) method. (Levey et al. *Ann Intern Med.* 1999; 130 (6):461-470). The NO PAIN and GenePAD studies were funded by the National Heart, Lung and Blood Institute (NHLBI), and approved and monitored by the Stanford University Committee for the Protection of Human Subjects.

Proteomic Profiling of Plasma Samples

Venipuncture was performed on fasting subjects and serum and plasma samples were stored at −75 Celsius. Plasma samples (20 µl) were denatured at pH 9 in a buffer containing 9 M urea, 2% (3-[(3-cholamidopropyl) dimethylammonio]-1-propane-sulfonate) and 50 mM Tris-HCL pH 9-0. The denatured sample was applied to a BioSepra Hyper Q DF anion exchange column. Proteins were eluted using buffers at pH 9, 7, 5, 4, 3 and organic solvent. All six fractions of each sample were applied to two types of PROTEINCHIP® arrays: immobilized metal affinity (IMAC30) chip, and a cationic exchange (CM10) chip. Protein array chips were analyzed by surface enhanced laser desorption/ionization time-of-flight mass spectrometry (SELDI-TOF). (Fung et al. *Biotechniques.* 2002; Suppl:34-38, 40-31).

SELDI-TOF was performed using a PROTEINCHIP® PCS4000 Mass Reader (Ciphergen Biosystems, Fremont Calif., USA) with established protocols (laser intensity 1600-7000 nJ with a sampling rate of 800 mHz). Protein peaks were identified from the raw spectrum data by applying a threshold to peak intensity analysis normalized against total ion current (using CIPHERGENEXPRESS™ Data Manager Software version 3-0).

Data Analyses and Statistics

Differences in peak intensities between groups were determined by applying Significance Analysis of Microarrays (SAM) (Tusher et al. *Proc Natl Acad SciUSA*. 2001; 98(9): 5116-5121). This analysis was confirmed by a second bioinformatics approach, Prediction Analysis for Microarrays (PAM) (Tibshirani et al. *Proc Natl Acad Sci USA*. 2002; 99(10):6567-6572). Differences between groups in the ELISA measurements were calculated by using independent t-test, one-way ANOVA corrected with Bonferroni method, or Mann-Whitney nonparametric test where appropriate. Correlations were analyzed using Spearman's nonparametric correlation analysis and multivariate regression was used for assessments of independence of correlations. A p value of <0-05 was taken to indicate statistical significance. Data was analyzed using SPSS software.

Confirmatory Biochemical Studies

A PROTEINCHIP®-array-based immunoassay using an anti-β2m antibody (Abcam, Cambridge, UK) was employed to specifically capture β2m from plasma samples. Subsequently, peak intensity was determined for each sample using SELDI-TOF. In addition, fractionated or non-fractionated plasma samples were subjected to a Western-blot analysis for β2m. Both fractionated plasma proteins (5 μg) and 0-4 μl of unfractionated plasma were electrophoresed on 8-16% gradient polyacrylamide, Tris-SDS gels (Bio-Rad, Hercules, Calif., USA) and transferred to a positively charged PVDF membrane. The presence of β2m was detected with rabbit anti-human β2m antibody conjugated with horse radish peroxidase (Abcam, Cambridge, UK) and a chemoluminescence protein detection kit (Amersham, Buckinghamshire, UK). Finally, β2m was measured by ELISA in plasma and serum samples using kits obtained from Immunodiagnostik (Bensheim, Germany) and R&D systems (Minneapolis, Minn. USA), respectively.

Patient Characteristics

In the initial discovery study, patients with PAD (n=45) had a greater prevalence of vascular risk factors than non-PAD subjects (n=43; Table 1) as expected. There were no differences between the groups in terms of gender, prevalence of diabetes, smoking history, kidney disease, BMI, or history of CAD.

In the confirmatory study, a second set of non-PAD (n=20) and PAD subjects (n=20) were well-matched for age and gender, although the risk factor burden remained higher in the PAD group (Table 1).

TABLE 1

Patient Demographics

| Discovery Study | PAD (n = 45) | No PAD (n = 43) | p value |
|---|---|---|---|
| Age (years) | 72.3 ± 8.9 | 66.0 ± 11.3 | <0.01 |
| Women (%) | 22 | 37 | 0.16 |
| Hypertension (%) | 80 | 59 | 0.04 |
| Hyperlipidemia (%) | 82 | 51 | <0.01 |
| Diabetes (%) | 24 | 17 | 0.44 |
| Smoking (%) | 81 | 62 | 0.14 |
| Index ABI | 0.60 ± 0.18 | 1.06 ± 0.10 | <0.01 |
| GFR (ml/min/1.73 m$^2$) | 66.5 ± 20.5 | 76.6 ± 12.2 | <0.01 |
| Body Mass Index (kg/m$^2$) | 28.8 ± 4.8 | 27.8 ± 6.0 | 0.39 |

| Confirmation Study | PAD (n = 20) | No PAD (n = 20) | p value |
|---|---|---|---|
| Age (years) | 72.3 ± 7.9 | 70.1 ± 5.2 | 0.31 |
| Women (%) | 25 | 25 | 1.00 |
| Hypertension (%) | 90 | 65 | 0.13 |
| Hyperlipidemia (%) | 85 | 30 | <0.01 |
| Diabetes (%) | 25 | 5 | 0.18 |
| Smoking (%) | 85 | 45 | 0.12 |
| Index ABI | 0.55 ± 0.22 | 1.15 ± 0.14 | <0.01 |

| Validation Study | No CAD/No PAD (n = 82) | CAD/No PAD (n = 80) | CAD/PAD (n = 75) |
|---|---|---|---|
| Age (years) | 63.4 ± 10.0* | 71.6 ± 9.3 | 71.7 ± 10.3 |
| Women (%) | 62* | 46 | 45 |
| Hypertension (%) | 74* | 87 | 87 |
| Hyperlipidemia (%) | 56* | 75 | 79 |
| Diabetes (%) | 22 | 28 | 48† |
| Smoking (%) | 42 | 51 | 65 |
| Index ABI | 1.06 ± 0.10 | 1.05 ± 0.09 | 0.68 ± 0.17§ |
| GFR (ml/min/1.73 m$^2$) | 94.8 ± 46.8* | 77.1 ± 34.2 | 72.6 ± 3.5 |
| BMI (kg/m$^2$) | 29.0 ± 6.1 | 28.6 ± 6.2 | 29.2 ± 5.8 |

*p < 0.05 between No CAD/No PAD and other two groups
†p < 0.05 between CAD/PAD and CAD/No PAD
§p < 0.05 between No CAD/No PAD and CAD/PAD In the third screening study, 237 subjects presenting for elective coronary angiography were included. In this study, patients with CAD with and without PAD were well matched for age, gender and risk factors (Table 1).

Example 1

High-Throughput Proteomics Analysis

In each subject in the discovery study, 1619 different protein peaks, arising from SELDI-TOF of using six different plasma fractions and two types of chips, were analyzed. SAM analysis revealed that of the 1619 peaks, there were 11 that had higher peak intensities in the PAD group (at a q value less than 10%; FIG. 1 and Table 2). Six of the 11 peaks around 12 kDa, obtained using different pH fractions, ProteinChip types, or energy states, were suspected to represent the same protein (Table 2). These peaks were identified as representing β2m as previously described. (Hampel et al. *J Am Soc Nephrol.* 2001; 12(5):1026-1035; Ishikawa et al. *Am J Nephrol.* 2006; 26(4):372-380). Other peaks found to be higher in the PAD group were 13 kDa and 15 kDa proteins identified as Cystatin C and Lysozyme C, respectively. Furthermore, unidentified proteins at 22 kDa and 36 kDa manifested higher levels in the PAD group.

TABLE 2

Linear Regression Between Peak Intensities and the ABI for Differentially Expressed Proteins in the Discovery Study

| | | | Mean Peak Intensities | | |
|---|---|---|---|---|---|
| m/Z | Conditions | Protein | PAD | No PAD | p |
| 11,732 | CM10-pH7 | Beta-2-microglobulin | 2.84 ± 0.17 | 2.03 ± 0.12 | <0.001 |
| 11,731 | CM10-pH7 | Beta-2-microglobulin | 9.90 ± 0.49 | 7.77 ± 0.45 | 0.002 |
| 11,722 | IMAC30-pH7 | Beta-2-microglobulin | 11.37 ± 0.72 | 8.64 ± 0.59 | 0.004 |
| 11,731 | IMAC30-pH5 | Beta-2-microglobulin | 13.88 ± 1.61 | 7.54 ± 0.48 | <0.001 |
| 11,811 | IMAC30-pH9 | Beta-2-microglobulin | 24.92 ± 0.88 | 21.21 ± 0.93 | 0.005 |
| 11,941 | IMAC30-pH5 | Beta-2-microglobulin, SPA adduct | 3.94 ± 0.35 | 2.54 ± 0.14 | <0.001 |
| 13,339 | CM10-pH9 | Cystatin C | 4.80 ± 0.29 | 3.66 ± 0.14 | 0.001 |
| 14,690 | CM10-pH9 | Lysozyme C | 2.98 ± 0.20 | 2.15 ± 0.15 | 0.02 |
| 22,519 | CM10-pH7 | Most likely IgG light chain | 2.81 ± 0.12 | 2.21 ± 0.14 | <0.001 |
| 22,999 | CM10-organic | Not determined | 6.58 ± 0.31 | 5.39 ± 0.25 | 0.004 |
| 36,067 | CM10-pH4 | Not determined | 0.48 ± 0.04 | 0.35 ± 0.02 | 0.003 |

Means were compared by student's t test

Example 2

Identification Of 12 kDA Protein as B2M

Figure 3:
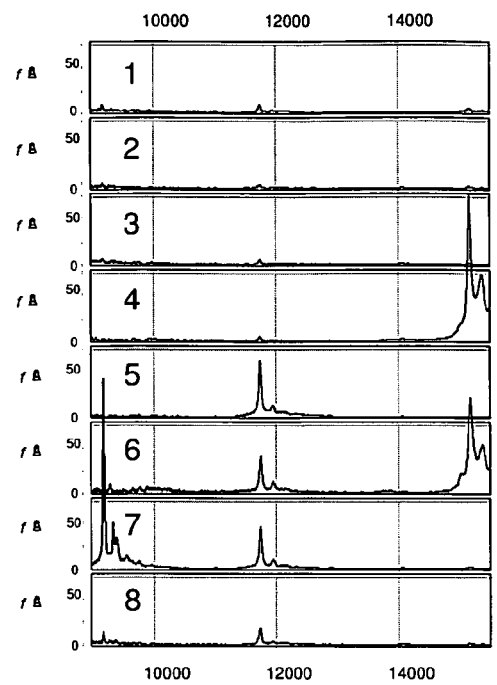
FIG. 3: Increased expression in PAD patients of a 12 kDa protein. SELDI TOF and Western blot analyses.
Figure 3:
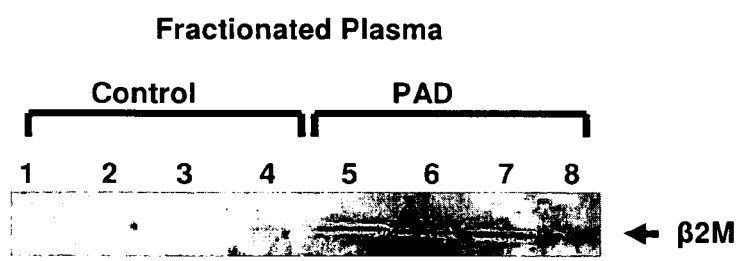
Figure 3:
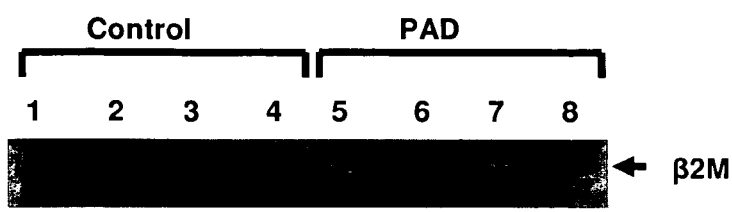

To confirm that the 12 kDa protein was β2m, a PROTEINCHIP®-array-based immunoassay and Western blot analyses were used. The immunoaffinity studies using anti-β2m antibody indicated that the 12 kDa peak was most likely β2m, based on the mass of the peak immunoprecipitated by the anti-β2m antibody. In addition, the 12 kDa peak could be immunodepleted by an anti-β2m antibody. Western blot analyses for β2m in fractionated or un-fractionated plasma from PAD patients and control subjects revealed expression levels that were generally consistent with the 12 kDa peak intensities, and which were higher in the subjects with PAD (FIG. 3, Panels A and B).

Figure 2A:
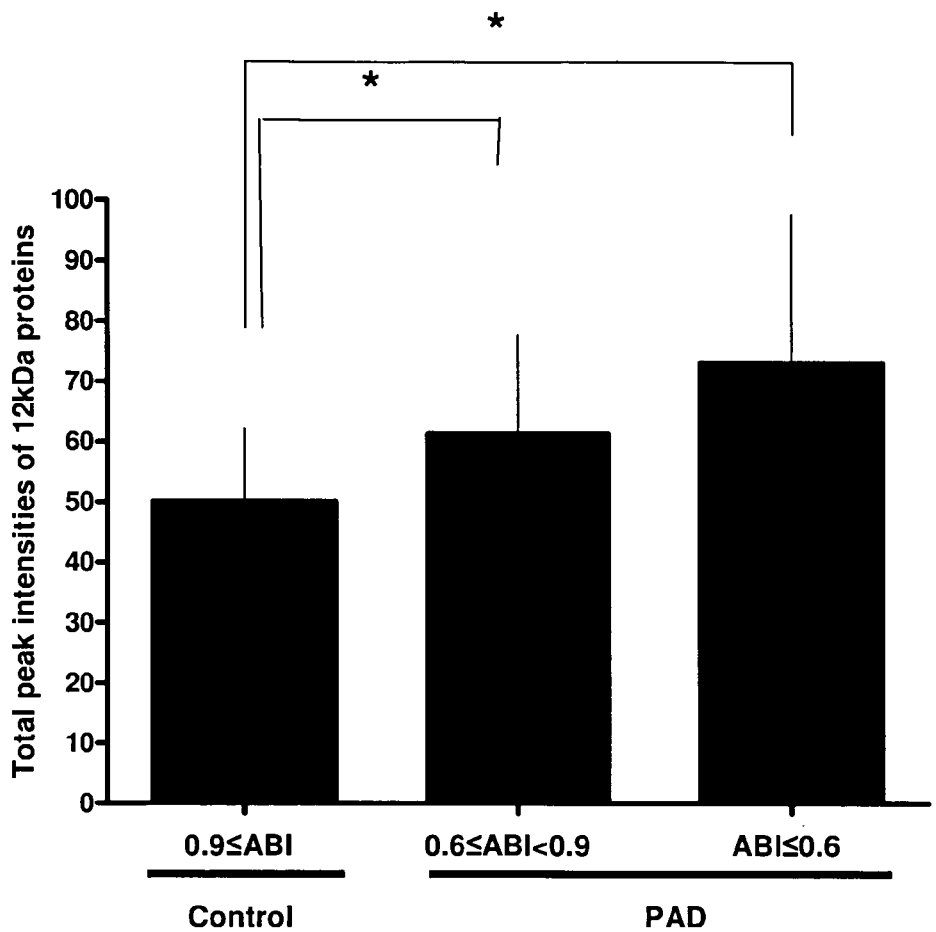
Figure 2B:
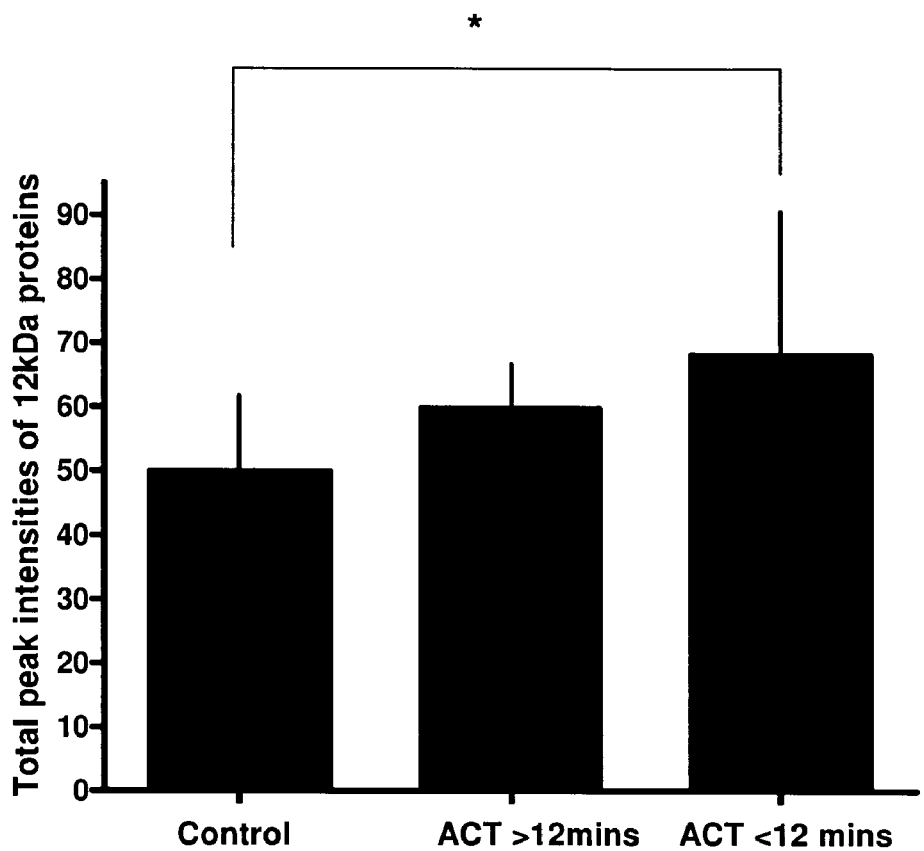

The peak intensities of the 12 kDa protein (putatively identified as β2m) were highly correlated with ABI (r=−0.49, p<0.001) (FIG. 2A). This finding indicated that the plasma level of β2m is correlated with the severity of PAD. Also, there was also a relationship with peak intensity of β2m when the subjects were divided into tertiles by absolute claudication time (ACT; groups being normal subjects without claudication; PAD with absolute ACT>12 minutes; or PAD with ACT<12 minutes; (FIG. 2B).

Example 3

Confirmation Study of B2M as a Biomarker for PAD

A confirmation study was performed in a separate set of age and gender matched subjects with (n=20) or without PAD (n=20). Plasma and serum β2m were measured by ELISA. The β2m levels were significantly higher in PAD patients than non-PAD subjects both in plasma (PAD=2-17+/−0-63 µg/ml, non-PAD=1-72+/−0-42 µg/ml, p=0.014) and serum (PAD=2-91+/−088 µg/ml, non-PAD=2-36+/−0-67 µg/ml, p=0-026). Plasma β2m levels were inversely correlated with ABI (r=0-727, p<0-001). Log-transformed plasma β2m (p=0-030) and smoking (p<0-001) were independent predictors of index ABI in this validation study. Plasma β2m levels correlated with hsCRP by univariate correlation (r=0.201, p<0.001) and this was independent of other risk factors by multivariate regression (Table 3). Other independent correlates for plasma β2m in our population included estimated GFR, diabetes, hyperlipidemia and body mass index) (Table 3).

TABLE 3

Independent Correlates of β 2 Microglobulin in Patients at Risk of Atherosclerosis

| | Standardized coefficients | p value |
|---|---|---|
| Age | −0.00 | 0.908 |
| Gender | −0.01 | 0.275 |
| Smoking | 0.09 | 0.080 |
| Diabetes | 0.14 | 0.005 |
| Hyperlipidemia | −0.21 | <0.001 |
| Hypertension | 0.08 | 0.114 |
| BMI | 0.24 | <0.001 |
| Log GFR | −0.73 | <0.001 |
| Log hsCRP | 0.19 | <0.001 |

Multivariate regression model; $R^2$ (adjusted) = 49% Significant correlates bolded

Example 4

Validation Study in a Population at Risk for Pad

In patients undergoing coronary angiography, (n=237), serum β2m was higher in patients with PAD. Also, the combination of β2m and hsCRP levels correlated with PAD diagnosis independent of other vascular risk factors and GFR by stepwise regression analysis (Table 4), consistent with the earlier observation in the smaller confirmation study. Increasing age and diagnosis of diabetes were the other independent correlates of PAD diagnosis.

TABLE 4

Predictors of Diagnosis of PAD in Patients at Risk of Atherosclerosis

| Model | Predictor | Standardized Coefficients | p value |
|---|---|---|---|
| 1 | β 2 M & hs CRP | 0.266 | <0.001 |
| 2 | β 2 M & hs CRP | 0.246 | <0.001 |
|   | Diabetes | 0.180 | 0.005 |
| 3 | β 2 M & hs CRP | 0.218 | 0.001 |
|   | Diabetes | 0.201 | 0.002 |
|   | Age | 0.172 | 0.007 |

Figure 4:
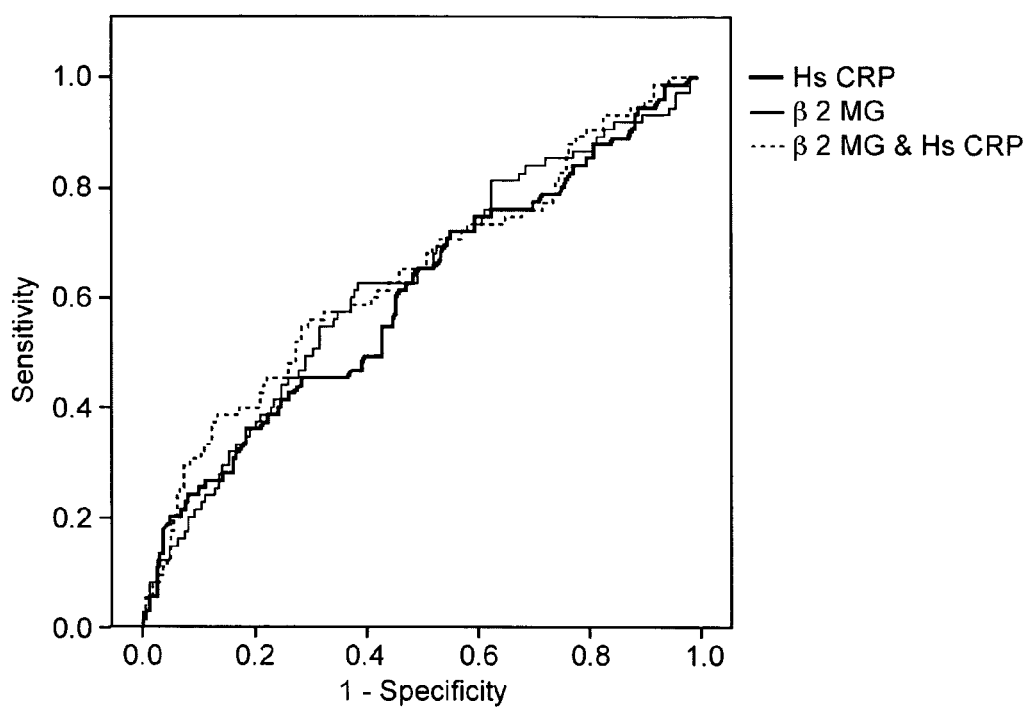
FIG. 4: Receiver Operator Curves for the Diagnosis of PAD using Assays for B2M, HsCRP or a Combination of the Two Assays. This figure presents data for combination test derived from logistic regression analysis using PAD defined ABI less than 0.9 as the dependent variable.

Stepwise regression model
PAD defined as an ankle brachial index <0.9
Other variables included in initial model: gender, body mass index, hypercholesterolemia, hypertension, pack years smoking, estimated glomerular filtration rate, high sensitivity c-reactive protein, β 2 microglobulin The odds ratio for the diagnosis of PAD for elevated β2m was 7.2 (95% Cl 1.6-31.3, p=0.009) and for hsCRP was 1.3 (1.0-1.7, p=0.026). We constructed receiver operator curves (ROC) for β2m, hsCRP and a combination of the two tests derived from logistic regression using PAD as the dependent variable (FIG. 4). Although the AUC for the assays used in isolation from other risk factors was modest, this showed that β2m and a combination with hsCRP were at least as predictive of PAD diagnosis in our cohort than hsCRP alone when comparing the areas under the curve.

Since increased plasma levels of β2m also occur in a variety of autoimmune, neoplastic and infectious diseases, including multiple myeloma, lymphoma and Sjogren's disease, analysis of both B2M and CRP can facilitate a differential diagnosis to facilitate assessment of PAD risk in such patient.

Example 5

Analysis of CRP and B2M Levels and Correlation to Pad Status

Because CRP and B2M levels were not normally distributed, subjects from Example 4 were divided based on median CRP levels and median B2M levels. The median CRP level in this study was 1.65 mg/dl (mean CRP level was 3.8 mg/dl). The median B2M level in this study was 1.677 mg/dl (mean B2M level was 2.1 mg/dl). Thus, subjects having a CRP level above 1.65 mg/dl were classified as "high CRP"; subjects having a CRP level below 1.65 mg/dl were classified as "low CRP". Similarly, subjects having a B2M level above 1.677 mg/dl were classified as "high B2M"; subjects having a B2M level below 1.677 mg/dl were classified as "low B2M".

Figure 5:
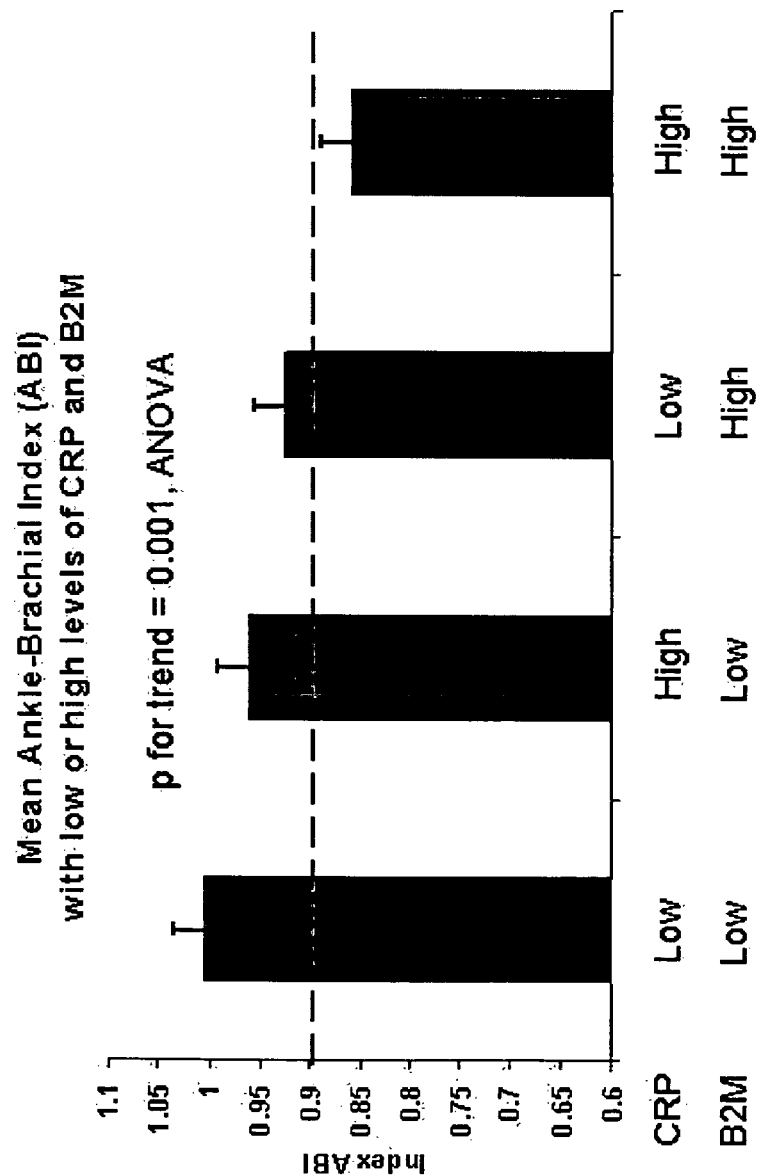
FIG. 5 is a graph showing correlation of ankle-brachial index (ABI) scores with B2M levels and CRP levels.

As shown in FIG. 5, high levels of either CRP or B2M were correlated with decreasing ABI scores, indicating an increased propensity toward PAD. Notably, high levels of both CRP and B2M were strongly correlated with an ABI score below 0.9 mg/dl, and thus strongly correlated with a diagnosis of PAD.

Using high throughput proteomic profiling, plasma B2M is elevated in patients with PAD, and is correlated with lower ABI and functional capacity. Use of the assay in diagnosing PAD in patients at high risk of atherosclerosis provided complementary data when both hsCRP and CRP assays were both used.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for diagnosing peripheral artery disease in a subject, the method comprising:
   detecting beta-2-microglobulin (B2M) and C-reactive protein (CRP) in a blood sample from a subject, wherein the subject has one or more cardiovascular disease symptoms or risk factors,
   wherein detection of B2M and CRP are indicative of a peripheral artery disease (PAD) in the subject.

2. The method of claim 1, wherein CRP and B2M are detected by immunoassay.

3. The method of claim 1, wherein CRP and B2M are detected by mass spectrometry.

4. The method of claim 1, wherein the blood sample is peripheral blood or a blood derivative.

5. The method of claim 1, wherein the CRP and B2M levels are analyzed by executing a software classification algorithm.

6. The method of claim 1, wherein the method further comprises reporting the diagnosis to the subject.

7. The method of claim 6, wherein said reporting comprises displaying the result to a user on a display.

8. The method of claim 1, wherein the method further comprises managing treatment of the subject in response to the PAD status.

9. The method of claim 1, wherein the subject has been diagnosed with coronary artery disease.

10. A method for diagnosing peripheral artery disease (PAD) in a subject having coronary artery disease (CAD), the method comprising:
    detecting a level of beta-2-microglobulin (B2M) in a biological sample from a subject, wherein the subject has one or more symptoms or risk factors common to peripheral artery disease (PAD) and coronary artery disease (CAD); and detecting a level of C-reactive protein (CRP) in the biological sample from the subject; wherein the levels of B2M and CRP detected are indicative of a diagnosis of PAD in the subject.

11. A method for assessing a course of peripheral artery disease comprising:
    detecting at a first time a level of beta-2-microglobulin (B2M) and a level of C reactive protein (CRP) in a first biological sample from a subject having peripheral artery disease (PAD);
    detecting at a second time a level of beta-2-microglobulin (B2M) and a level of C reactive protein (CRP) in a second biological sample from a subject;
    wherein the presence of absence of an increase or decrease in the B2M and CRP levels at said second time relative to said first time is indicative of the course of the peripheral artery disease.

* * * * *